(12) United States Patent
Bartlett et al.

(10) Patent No.: US 7,435,586 B2
(45) Date of Patent: Oct. 14, 2008

(54) METHOD OF PURIFICATION OF CELLS

(75) Inventors: Perry Francis Bartlett, North Carlton (AU); Rodney Lee Rietze, Brunswick (AU)

(73) Assignee: The University of Queensland, Queensland (AU)

( * ) Notice: Subject to any disclaimer, the term of this patent is extended or adjusted under 35 U.S.C. 154(b) by 389 days.

(21) Appl. No.: 10/479,306

(22) PCT Filed: May 31, 2002

(86) PCT No.: PCT/AU02/00700

§ 371 (c)(1),
(2), (4) Date: Jun. 29, 2004

(87) PCT Pub. No.: WO02/097067

PCT Pub. Date: Dec. 5, 2002

(65) Prior Publication Data

US 2004/0235158 A1 Nov. 25, 2004

(30) Foreign Application Priority Data

Jun. 1, 2001 (AU) .................................... PR5403

(51) Int. Cl.
*C12N 5/00* (2006.01)
*C12N 5/06* (2006.01)
(52) U.S. Cl. ..................... 435/325; 435/378; 435/368
(58) Field of Classification Search .................. None
See application file for complete search history.

(56) References Cited

U.S. PATENT DOCUMENTS

2003/0040119 A1* 2/2003 Takayama et al. ............. 436/63

FOREIGN PATENT DOCUMENTS

| WO | WO 00/47762 | 8/2000 |
| WO | WO 00/52143 | 9/2000 |

OTHER PUBLICATIONS

Morrison et al., Cell. Mar. 5, 1999;96(5):737-749.*

McLaren F.H. et al., "Analysis of Neural Stem Cells by Flow Cytometry: Cellular Differentiation Modifies Patterns of MHC Expression", *Journal of Neuroimmunology*, 112(1-2):35-46 (2001), XP002359031.
Osmond D.G. et al., "Pre-B Cells in Mouse Bone Marrow: In Vitro Maturation of Peanut Agglutinin Binding B Lymphocyte Precursors Separated from Bone Marrow by Fluorescence-Activated Cell Sorting", *The Journal of Immunology*, 133(1):86-90 (1984), XP002359032.
Rietze R.L. et al., "Purification of a Pluripotent Neural Stem Cell from the Adult Mouse Brain", *Nature* 412(6848):736-739 (2001).
Uchida N. et al., "Direct Isolation of Human Central Nervous System Stem Cells", *Proceeding of the National Academy of Sciences of the USA* 97(26):14720-14725 (2000).

* cited by examiner

*Primary Examiner*—David Romeo
*Assistant Examiner*—Daniel C Gamett
(74) *Attorney, Agent, or Firm*—Scully, Scott, Murphy & Presser, P.C.

(57) ABSTRACT

The present invention relates generally to a method for the generation of a substantially homogeneous population of undifferentiated cells. More particularly, the present invention relates to the purification of a substantially homogeneous population of stem cells and their progenitor or precursor cells. Even more particularly, the present invention provides a population of neural stem cells (NSCs). The subject invention is particularly directed to NSCs and precursor cells with the capacity to differentiate into cells and cell lineages required for the development, maintenance or repair of the central nervous system in an animal such as a mammal. The present invention is further directed to NSCs and progenitor and/or precursor cells which are capable of proliferation and differentiation into multiple cell lineages, such as but not limited to neurons, oligodendrocytes, glia and astrocytes. The subject invention further contemplates the use of NSCs and/or precursor cells for the repair or regeneration of tissue, such as tissue associated with the central nervous system, in an animal including a mammal. The NSCs of the present invention may be used to identify naturally occurring molecules such as cytokines as well as molecules obtained from natural product screening or screening of chemical libraries which induce proliferation of the NSCs. Such molecules are useful in the development of therapeutics.

4 Claims, 7 Drawing Sheets

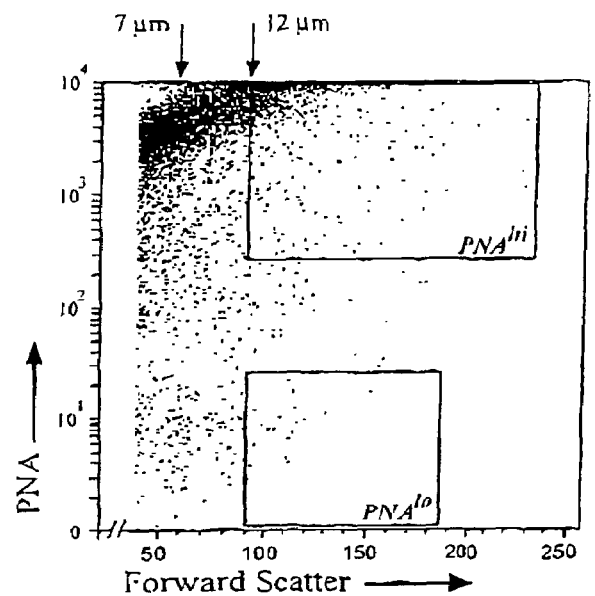
Figure 1A
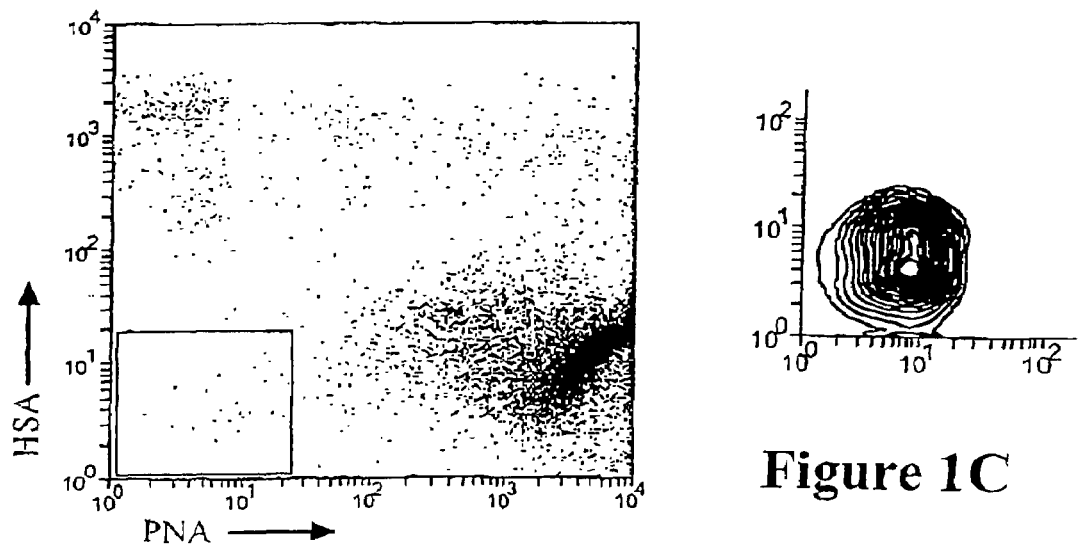
Figure 1C
Figure 1B

R1: 0.79%   R2: 15.3%

R3: 0.12%   R4: 0.24%   R5: 14.9%

SEQUENCE LISTING

<160> NUMBER OF SEQ ID NOS: 86

<210> SEQ ID NO 1
<211> LENGTH: 24
<212> TYPE: DNA
<213> ORGANISM: artificial sequence
<220> FEATURE:
<221> NAME/KEY: misc_feature
<222> LOCATION: ()..()
<223> OTHER INFORMATION: mbeta-actin (sense)

<400> SEQUENCE: 1
ctgaagtacc ccattgaaca tggc                                          24

<210> SEQ ID NO 2
<211> LENGTH: 24
<212> TYPE: DNA
<213> ORGANISM: artificial sequence
<220> FEATURE:
<221> NAME/KEY: misc_feature
<222> LOCATION: ()..()
<223> OTHER INFORMATION: mbeta-actin (antisense)

<400> SEQUENCE: 2
cagagcagta atctccttct gcat                                          24

<210> SEQ ID NO 3
<211> LENGTH: 22
<212> TYPE: DNA
<213> ORGANISM: artificial sequence
<220> FEATURE:
<221> NAME/KEY: misc_feature
<222> LOCATION: ()..()
<223> OTHER INFORMATION: hbeta-actin (sense)

<400> SEQUENCE: 3
accgcgagaa gatgacccag at                                          22

<210> SEQ ID NO 4
<211> LENGTH: 22
<212> TYPE: DNA
<213> ORGANISM: artificial sequence
<220> FEATURE:
<221> NAME/KEY: misc_feature
<222> LOCATION: ()..()
<223> OTHER INFORMATION: hbeta-actin (antisense)

<400> SEQUENCE: 4
caccttcacc gttccagttt tt                                          22

<210> SEQ ID NO 5
<211> LENGTH: 24
<212> TYPE: DNA
<213> ORGANISM: artificial sequence
<220> FEATURE:
<221> NAME/KEY: misc_feature
<222> LOCATION: ()..()
<223> OTHER INFORMATION: mEphA4 (sense)

<400> SEQUENCE: 5
gccaaagaaa tcgatgcatc ctgc                                        24

<210> SEQ ID NO 6
<211> LENGTH: 24
<212> TYPE: DNA
<213> ORGANISM: artificial sequence
<220> FEATURE:
<221> NAME/KEY: misc_feature
<222> LOCATION: ()..()
<223> OTHER INFORMATION: mEphA4 (antisense)

<400> SEQUENCE: 6
gacgctgctc aaaatcttat tctg                                        24

<210> SEQ ID NO 7
<211> LENGTH: 21
<212> TYPE: DNA
<213> ORGANISM: artificial sequence
<220> FEATURE:
<221> NAME/KEY: misc_feature
<222> LOCATION: ()..()
<223> OTHER INFORMATION: mDCC (sense)

<400> SEQUENCE: 7
cccagtccaa ggttacagat t                                           21

<210> SEQ ID NO 8
<211> LENGTH: 20
<212> TYPE: DNA
<213> ORGANISM: artificial sequence
<220> FEATURE:
<221> NAME/KEY: misc_feature
<222> LOCATION: ()..()
<223> OTHER INFORMATION: mDCC (antisense)

```
<400> SEQUENCE: 8
gaggtgtcca actcatgatg                                          20

<210> SEQ ID NO 9
<211> LENGTH: 21
<212> TYPE: DNA
<213> ORGANISM: artificial sequence
<220> FEATURE:
<221> NAME/KEY: misc_feature
<222> LOCATION: ()..()
<223> OTHER INFORMATION: mRyk (sense)

<400> SEQUENCE: 9
gccacaaagt tgttcacttg g                                        21

<210> SEQ ID NO 10
<211> LENGTH: 20
<212> TYPE: DNA
<213> ORGANISM: artificial sequence
<220> FEATURE:
<221> NAME/KEY: misc_feature
<222> LOCATION: ()..()
<223> OTHER INFORMATION: mRyk (antisense)

<400> SEQUENCE: 10
gctgacacac ccaacaatgc                                          20

<210> SEQ ID NO 11
<211> LENGTH: 20
<212> TYPE: DNA
<213> ORGANISM: artificial sequence
<220> FEATURE:
<221> NAME/KEY: misc_feature
<222> LOCATION: ()..()
<223> OTHER INFORMATION: mNeogenin splice #1 (sense)

<400> SEQUENCE: 11
gggggatgtg gttatcccca                                          20

<210> SEQ ID NO 12
<211> LENGTH: 21
<212> TYPE: DNA
<213> ORGANISM: artificial sequence
<220> FEATURE:
<221> NAME/KEY: misc_feature
<222> LOCATION: ()..()
<223> OTHER INFORMATION: mNeogenin splice #1 (antisense)

<400> SEQUENCE: 12
gatgcaggtg tacgccatgt c                                        21

<210> SEQ ID NO 13
<211> LENGTH: 21
<212> TYPE: DNA
<213> ORGANISM: artificial sequence
<220> FEATURE:
<221> NAME/KEY: misc_feature
<222> LOCATION: ()..()
<223> OTHER INFORMATION: mNeogenin splice #2 (sense)

<400> SEQUENCE: 13
ggcgaaggca tcccccttta t                                        21

<210> SEQ ID NO 14
<211> LENGTH: 21
<212> TYPE: DNA
<213> ORGANISM: artificial sequence
```

```
<220> FEATURE:
<221> NAME/KEY: misc_feature
<222> LOCATION: ()..()
<223> OTHER INFORMATION: mNeogenin splice #2 (antisense)

<400> SEQUENCE: 14
gggagttgtc tgcccaggta a                                              21

<210> SEQ ID NO 15
<211> LENGTH: 21
<212> TYPE: DNA
<213> ORGANISM: artificial sequence
<220> FEATURE:
<221> NAME/KEY: misc_feature
<222> LOCATION: ()..()
<223> OTHER INFORMATION: mNeogenin splice #4 (sense)

<400> SEQUENCE: 15
agggcatgag tcagaggaca g                                              21

<210> SEQ ID NO 16
<211> LENGTH: 21
<212> TYPE: DNA
<213> ORGANISM: artificial sequence
<220> FEATURE:
<221> NAME/KEY: misc_feature
<222> LOCATION: ()..()
<223> OTHER INFORMATION: mNeogenin splice #4 (antisense)

<400> SEQUENCE: 16
agtcttcctc ttgggagctg g                                              21

<210> SEQ ID NO 17
<211> LENGTH: 20
<212> TYPE: DNA
<213> ORGANISM: artificial sequence
<220> FEATURE:
<221> NAME/KEY: misc_feature
<222> LOCATION: ()..()
<223> OTHER INFORMATION: mTrkA (sense)

<400> SEQUENCE: 17
tgcgctggtt gttcaacggc                                                20

<210> SEQ ID NO 18
<211> LENGTH: 20
<212> TYPE: DNA
<213> ORGANISM: artificial sequence
<220> FEATURE:
<221> NAME/KEY: misc_feature
<222> LOCATION: ()..()
<223> OTHER INFORMATION: mTrkA (antisense)

<400> SEQUENCE: 18
cccacttgag aatgatgtcc                                                20

<210> SEQ ID NO 19
<211> LENGTH: 20
<212> TYPE: DNA
<213> ORGANISM: artificial sequence
<220> FEATURE:
<221> NAME/KEY: misc_feature
<222> LOCATION: ()..()
<223> OTHER INFORMATION: mTrkB (sense)

<400> SEQUENCE: 19
acacacaggg ctccttaagg                                                20
```

```
<210> SEQ ID NO 20
<211> LENGTH: 20
<212> TYPE: DNA
<213> ORGANISM: artificial sequence
<220> FEATURE:
<221> NAME/KEY: misc_feature
<222> LOCATION: ()..()
<223> OTHER INFORMATION: mTrkB (antisense)

<400> SEQUENCE: 20
catagaccga gagatgctcc                                              20

<210> SEQ ID NO 21
<211> LENGTH: 20
<212> TYPE: DNA
<213> ORGANISM: artificial sequence
<220> FEATURE:
<221> NAME/KEY: misc_feature
<222> LOCATION: ()..()
<223> OTHER INFORMATION: mTrkC (sense)

<400> SEQUENCE: 21
tgccatcaac ttgaccctcg                                              20

<210> SEQ ID NO 22
<211> LENGTH: 20
<212> TYPE: DNA
<213> ORGANISM: artificial sequence
<220> FEATURE:
<221> NAME/KEY: misc_feature
<222> LOCATION: ()..()
<223> OTHER INFORMATION: mTrkC (antisense)

<400> SEQUENCE: 22
agcaagtccg actgctatgg                                              20

<210> SEQ ID NO 23
<211> LENGTH: 20
<212> TYPE: DNA
<213> ORGANISM: artificial sequence
<220> FEATURE:
<221> NAME/KEY: misc_feature
<222> LOCATION: ()..()
<223> OTHER INFORMATION: mp75 (sense)

<400> SEQUENCE: 23
gtgcaccgag tgcctgggcc                                              20

<210> SEQ ID NO 24
<211> LENGTH: 20
<212> TYPE: DNA
<213> ORGANISM: artificial sequence
<220> FEATURE:
<221> NAME/KEY: misc_feature
<222> LOCATION: ()..()
<223> OTHER INFORMATION: mp75 (antisense)

<400> SEQUENCE: 24
cacagcagcc aagatggagc                                              20

<210> SEQ ID NO 25
<211> LENGTH: 19
<212> TYPE: DNA
<213> ORGANISM: artificial sequence
<220> FEATURE:
<221> NAME/KEY: misc_feature
<222> LOCATION: ()..()
<223> OTHER INFORMATION: mLIFRbeta (sense)
```

<400> SEQUENCE: 25
gctgtcattg ttggcgtgg                                                    19

<210> SEQ ID NO 26
<211> LENGTH: 23
<212> TYPE: DNA
<213> ORGANISM: artificial sequence
<220> FEATURE:
<221> NAME/KEY: misc_feature
<222> LOCATION: ()..()
<223> OTHER INFORMATION: mLIFRbeta (antisense)

<400> SEQUENCE: 26
ttcatttcca atgttttaag agc                                               23

<210> SEQ ID NO 27
<211> LENGTH: 24
<212> TYPE: DNA
<213> ORGANISM: artificial sequence
<220> FEATURE:
<221> NAME/KEY: misc_feature
<222> LOCATION: ()..()
<223> OTHER INFORMATION: mgp130 (sense)

<400> SEQUENCE: 27
gcccttggga atgtctcctc agag                                              24

<210> SEQ ID NO 28
<211> LENGTH: 24
<212> TYPE: DNA
<213> ORGANISM: artificial sequence
<220> FEATURE:
<221> NAME/KEY: misc_feature
<222> LOCATION: ()..()
<223> OTHER INFORMATION: mgp130 (antisense)

<400> SEQUENCE: 28
tcttccatat gagccgtgca gacc                                              24

<210> SEQ ID NO 29
<211> LENGTH: 20
<212> TYPE: DNA
<213> ORGANISM: artificial sequence
<220> FEATURE:
<221> NAME/KEY: misc_feature
<222> LOCATION: ()..()
<223> OTHER INFORMATION: mNR6 (sense)

<400> SEQUENCE: 29
ggatcgggag cccacacagc                                                   20

<210> SEQ ID NO 30
<211> LENGTH: 20
<212> TYPE: DNA
<213> ORGANISM: artificial sequence
<220> FEATURE:
<221> NAME/KEY: misc_feature
<222> LOCATION: ()..()
<223> OTHER INFORMATION: mNR6 (antisense)

<400> SEQUENCE: 30
agcggcacgt gagatccttc                                                   20

<210> SEQ ID NO 31
<211> LENGTH: 25
<212> TYPE: DNA
<213> ORGANISM: artificial sequence

```
<220> FEATURE:
<221> NAME/KEY: misc_feature
<222> LOCATION: ()..()
<223> OTHER INFORMATION: mNotch1 (sense)

<400> SEQUENCE: 31
ttacagccac catcacagcc acacc                                      25

<210> SEQ ID NO 32
<211> LENGTH: 20
<212> TYPE: DNA
<213> ORGANISM: artificial sequence
<220> FEATURE:
<221> NAME/KEY: misc_feature
<222> LOCATION: ()..()
<223> OTHER INFORMATION: mNotch 1 (antisense)

<400> SEQUENCE: 32
atgccctcgg accaatcaga                                            20

<210> SEQ ID NO 33
<211> LENGTH: 25
<212> TYPE: DNA
<213> ORGANISM: artificial sequence
<220> FEATURE:
<221> NAME/KEY: misc_feature
<222> LOCATION: ()..()
<223> OTHER INFORMATION: mNotch 2 (sense)

<400> SEQUENCE: 33
gaggcgactc ttctgctgtt gaaga                                      25

<210> SEQ ID NO 34
<211> LENGTH: 25
<212> TYPE: DNA
<213> ORGANISM: artificial sequence
<220> FEATURE:
<221> NAME/KEY: misc_feature
<222> LOCATION: ()..()
<223> OTHER INFORMATION: mNotch2 (antisense)

<400> SEQUENCE: 34
atagagtcac tgagctctcg gacag                                      25

<210> SEQ ID NO 35
<211> LENGTH: 18
<212> TYPE: DNA
<213> ORGANISM: artificial sequence
<220> FEATURE:
<221> NAME/KEY: misc_feature
<222> LOCATION: ()..()
<223> OTHER INFORMATION: mNotch3 (sense)

<400> SEQUENCE: 35
acactgggag ttctctgt                                              18

<210> SEQ ID NO 36
<211> LENGTH: 18
<212> TYPE: DNA
<213> ORGANISM: artificial sequence
<220> FEATURE:
<221> NAME/KEY: misc_feature
<222> LOCATION: ()..()
<223> OTHER INFORMATION: mNotch3 (antisense)

<400> SEQUENCE: 36
gtctgctggc atgggata                                              18
```

```
<210> SEQ ID NO 37
<211> LENGTH: 25
<212> TYPE: DNA
<213> ORGANISM: artificial sequence
<220> FEATURE:
<221> NAME/KEY: misc_feature
<222> LOCATION: ()..()
<223> OTHER INFORMATION: mdelta1 (sense)

<400> SEQUENCE: 37
tgtgacgagg actactacgg agaag                                    25

<210> SEQ ID NO 38
<211> LENGTH: 25
<212> TYPE: DNA
<213> ORGANISM: artificial sequence
<220> FEATURE:
<221> NAME/KEY: misc_feature
<222> LOCATION: ()..()
<223> OTHER INFORMATION: mdelta1 (antisense)

<400> SEQUENCE: 38
agtagttcag gtcttggttg cagaa                                    25

<210> SEQ ID NO 39
<211> LENGTH: 24
<212> TYPE: DNA
<213> ORGANISM: artificial sequence
<220> FEATURE:
<221> NAME/KEY: misc_feature
<222> LOCATION: ()..()
<223> OTHER INFORMATION: mSOCS1 (sense)

<400> SEQUENCE: 39
ctcgagtagg atggtagcac gcaa                                     24

<210> SEQ ID NO 40
<211> LENGTH: 24
<212> TYPE: DNA
<213> ORGANISM: artificial sequence
<220> FEATURE:
<221> NAME/KEY: misc_feature
<222> LOCATION: ()..()
<223> OTHER INFORMATION: mSOCS1 (antisense)

<400> SEQUENCE: 40
catcttcacg ctgagcgcga agaa                                     24

<210> SEQ ID NO 41
<211> LENGTH: 20
<212> TYPE: DNA
<213> ORGANISM: artificial sequence
<220> FEATURE:
<221> NAME/KEY: misc_feature
<222> LOCATION: ()..()
<223> OTHER INFORMATION: mSOCS2 (sense)

<400> SEQUENCE: 41
ggaatggagc ggacaggacg                                          20

<210> SEQ ID NO 42
<211> LENGTH: 22
<212> TYPE: DNA
<213> ORGANISM: artificial sequence
<220> FEATURE:
<221> NAME/KEY: misc_feature
<222> LOCATION: ()..()
<223> OTHER INFORMATION: mSOCS2 (antisense)
```

```
<400> SEQUENCE: 42
gtactcaatc cgcaggttag tc                                              22

<210> SEQ ID NO 43
<211> LENGTH: 20
<212> TYPE: DNA
<213> ORGANISM: artificial sequence
<220> FEATURE:
<221> NAME/KEY: misc_feature
<222> LOCATION: ()..()
<223> OTHER INFORMATION: mSOCS3 (sense)

<400> SEQUENCE: 43
accagcgcca cttcttcacg                                                 20

<210> SEQ ID NO 44
<211> LENGTH: 20
<212> TYPE: DNA
<213> ORGANISM: artificial sequence
<220> FEATURE:
<221> NAME/KEY: misc_feature
<222> LOCATION: ()..()
<223> OTHER INFORMATION: mSOCS3 (antisense)

<400> SEQUENCE: 44
gtggagcatc atactgatcc                                                 20

<210> SEQ ID NO 45
<211> LENGTH: 21
<212> TYPE: DNA
<213> ORGANISM: artificial sequence
<220> FEATURE:
<221> NAME/KEY: misc_feature
<222> LOCATION: ()..()
<223> OTHER INFORMATION: mPax6 (sense)

<400> SEQUENCE: 45
aagtccaggt gctggacaat g                                               21

<210> SEQ ID NO 46
<211> LENGTH: 20
<212> TYPE: DNA
<213> ORGANISM: artificial sequence
<220> FEATURE:
<221> NAME/KEY: misc_feature
<222> LOCATION: ()..()
<223> OTHER INFORMATION: mPax6 (antisense)

<400> SEQUENCE: 46
gctgtgggat tggctggtag                                                 20

<210> SEQ ID NO 47
<211> LENGTH: 24
<212> TYPE: DNA
<213> ORGANISM: artificial sequence
<220> FEATURE:
<221> NAME/KEY: misc_feature
<222> LOCATION: ()..()
<223> OTHER INFORMATION: hPax6 (sense)

<400> SEQUENCE: 47
ctccacccgg cagaagattg taga                                            24

<210> SEQ ID NO 48
<211> LENGTH: 20
<212> TYPE: DNA
<213> ORGANISM: artificial sequence
```

```
<220> FEATURE:
<221> NAME/KEY: misc_feature
<222> LOCATION: ()..()
<223> OTHER INFORMATION: hPax6 (antisense)

<400> SEQUENCE: 48
ccggtgtggt gggttgtgga                                               20

<210> SEQ ID NO 49
<211> LENGTH: 21
<212> TYPE: DNA
<213> ORGANISM: artificial sequence
<220> FEATURE:
<221> NAME/KEY: misc_feature
<222> LOCATION: ()..()
<223> OTHER INFORMATION: mTbr1 (sense)

<400> SEQUENCE: 49
ctgactccaa ggactcacca g                                             21

<210> SEQ ID NO 50
<211> LENGTH: 20
<212> TYPE: DNA
<213> ORGANISM: artificial sequence
<220> FEATURE:
<221> NAME/KEY: misc_feature
<222> LOCATION: ()..()
<223> OTHER INFORMATION: mTbr1 (antisense)

<400> SEQUENCE: 50
tccagtgagc cccagtgttg                                               20

<210> SEQ ID NO 51
<211> LENGTH: 22
<212> TYPE: DNA
<213> ORGANISM: artificial sequence
<220> FEATURE:
<221> NAME/KEY: misc_feature
<222> LOCATION: ()..()
<223> OTHER INFORMATION: hTbr1 (sense)

<400> SEQUENCE: 51
cccgcctgca tgtggtggaa gt                                            22

<210> SEQ ID NO 52
<211> LENGTH: 22
<212> TYPE: DNA
<213> ORGANISM: artificial sequence
<220> FEATURE:
<221> NAME/KEY: misc_feature
<222> LOCATION: ()..()
<223> OTHER INFORMATION: hTbr1 (antisense)

<400> SEQUENCE: 52
gggcggccta gctgtgcgag ta                                            22

<210> SEQ ID NO 53
<211> LENGTH: 20
<212> TYPE: DNA
<213> ORGANISM: artificial sequence
<220> FEATURE:
<221> NAME/KEY: misc_feature
<222> LOCATION: ()..()
<223> OTHER INFORMATION: mSvet1 (sense)

<400> SEQUENCE: 53
ccctctggcg gtatagggaa                                               20
```

```
<210> SEQ ID NO 54
<211> LENGTH: 21
<212> TYPE: DNA
<213> ORGANISM: artificial sequence
<220> FEATURE:
<221> NAME/KEY: misc_feature
<222> LOCATION: ()..()
<223> OTHER INFORMATION: mSvet1 (antisense)

<400> SEQUENCE: 54
ggcctcttcc tctcatacct g                                        21

<210> SEQ ID NO 55
<211> LENGTH: 20
<212> TYPE: DNA
<213> ORGANISM: artificial sequence
<220> FEATURE:
<221> NAME/KEY: misc_feature
<222> LOCATION: ()..()
<223> OTHER INFORMATION: mNkx2.1 (sense)

<400> SEQUENCE: 55
gacgtgagca agaacatggc                                          20

<210> SEQ ID NO 56
<211> LENGTH: 19
<212> TYPE: DNA
<213> ORGANISM: artificial sequence
<220> FEATURE:
<221> NAME/KEY: misc_feature
<222> LOCATION: ()..()
<223> OTHER INFORMATION: mNkx2.1 (antisense)

<400> SEQUENCE: 56
gctggagacc tggccctgc                                           19

<210> SEQ ID NO 57
<211> LENGTH: 26
<212> TYPE: DNA
<213> ORGANISM: artificial sequence
<220> FEATURE:
<221> NAME/KEY: misc_feature
<222> LOCATION: ()..()
<223> OTHER INFORMATION: mDlx1 (sense)

<400> SEQUENCE: 57
aagaacacct ggccaagaag aaaaat                                   26

<210> SEQ ID NO 58
<211> LENGTH: 23
<212> TYPE: DNA
<213> ORGANISM: artificial sequence
<220> FEATURE:
<221> NAME/KEY: misc_feature
<222> LOCATION: ()..()
<223> OTHER INFORMATION: mDlx1 (antisense)

<400> SEQUENCE: 58
cccccaagat acaaagcaat aag                                      23

<210> SEQ ID NO 59
<211> LENGTH: 25
<212> TYPE: DNA
<213> ORGANISM: artificial sequence
<220> FEATURE:
<221> NAME/KEY: misc_feature
<222> LOCATION: ()..()
<223> OTHER INFORMATION: mDlx2 (sense)
```

```
<400> SEQUENCE: 59
aacactcccg tagctccttc atcca                                           25

<210> SEQ ID NO 60
<211> LENGTH: 24
<212> TYPE: DNA
<213> ORGANISM: artificial sequence
<220> FEATURE:
<221> NAME/KEY: misc_feature
<222> LOCATION: ()..()
<223> OTHER INFORMATION: mDlx2 (antisense)

<400> SEQUENCE: 60
ctacgtcgca gctttcacaa ctcg                                            24

<210> SEQ ID NO 61
<211> LENGTH: 21
<212> TYPE: DNA
<213> ORGANISM: artificial sequence
<220> FEATURE:
<221> NAME/KEY: misc_feature
<222> LOCATION: ()..()
<223> OTHER INFORMATION: mSox1 (sense)

<400> SEQUENCE: 61
gccgcgccgc aagaccaaga c                                               21

<210> SEQ ID NO 62
<211> LENGTH: 24
<212> TYPE: DNA
<213> ORGANISM: artificial sequence
<220> FEATURE:
<221> NAME/KEY: misc_feature
<222> LOCATION: ()..()
<223> OTHER INFORMATION: mSox1 (antisense)

<400> SEQUENCE: 62
cgccgtaagg gatgccgccg tagc                                            24

<210> SEQ ID NO 63
<211> LENGTH: 20
<212> TYPE: DNA
<213> ORGANISM: artificial sequence
<220> FEATURE:
<221> NAME/KEY: misc_feature
<222> LOCATION: ()..()
<223> OTHER INFORMATION: mSox2 (sense)

<400> SEQUENCE: 63
cgggggcagc ggcgtaagat                                                 20

<210> SEQ ID NO 64
<211> LENGTH: 20
<212> TYPE: DNA
<213> ORGANISM: artificial sequence
<220> FEATURE:
<221> NAME/KEY: misc_feature
<222> LOCATION: ()..()
<223> OTHER INFORMATION: mSox1 (antisense)

<400> SEQUENCE: 64
gggtgccctg ctgcgagtag                                                 20

<210> SEQ ID NO 65
<211> LENGTH: 20
<212> TYPE: DNA
<213> ORGANISM: artificial sequence
```

```
<220> FEATURE:
<221> NAME/KEY: misc_feature
<222> LOCATION: ()..()
<223> OTHER INFORMATION: mEmx1 (sense)

<400> SEQUENCE: 65
aatcactacg tggtgggagc                                              20

<210> SEQ ID NO 66
<211> LENGTH: 20
<212> TYPE: DNA
<213> ORGANISM: artificial sequence
<220> FEATURE:
<221> NAME/KEY: misc_feature
<222> LOCATION: ()..()
<223> OTHER INFORMATION: mEmx1 (antisense)

<400> SEQUENCE: 66
cccttcctct tccagcttct                                              20

<210> SEQ ID NO 67
<211> LENGTH: 24
<212> TYPE: DNA
<213> ORGANISM: artificial sequence
<220> FEATURE:
<221> NAME/KEY: misc_feature
<222> LOCATION: ()..()
<223> OTHER INFORMATION: hEmx1 (sense)

<400> SEQUENCE: 67
cgtgttcccc gaggccatga acca                                         24

<210> SEQ ID NO 68
<211> LENGTH: 24
<212> TYPE: DNA
<213> ORGANISM: artificial sequence
<220> FEATURE:
<221> NAME/KEY: misc_feature
<222> LOCATION: ()..()
<223> OTHER INFORMATION: hEmx1 (antisense)

<400> SEQUENCE: 68
gatgtcctcc ccattggcct gctt                                         24

<210> SEQ ID NO 69
<211> LENGTH: 25
<212> TYPE: DNA
<213> ORGANISM: artificial sequence
<220> FEATURE:
<221> NAME/KEY: misc_feature
<222> LOCATION: ()..()
<223> OTHER INFORMATION: mEmx2 #1 (sense)

<400> SEQUENCE: 69
ccgagagttt ccttttgcac aacgc                                        25

<210> SEQ ID NO 70
<211> LENGTH: 25
<212> TYPE: DNA
<213> ORGANISM: artificial sequence
<220> FEATURE:
<221> NAME/KEY: misc_feature
<222> LOCATION: ()..()
<223> OTHER INFORMATION: mEmx2 #1 (antisense)

<400> SEQUENCE: 70
gcctgcttgg tagcaattct ccacc                                        25
```

```
<210> SEQ ID NO 71
<211> LENGTH: 20
<212> TYPE: DNA
<213> ORGANISM: artificial sequence
<220> FEATURE:
<221> NAME/KEY: misc_feature
<222> LOCATION: ()..()
<223> OTHER INFORMATION: mEmx2 #2 (sense)

<400> SEQUENCE: 71
cccagctttt aaggctagag                                              20

<210> SEQ ID NO 72
<211> LENGTH: 20
<212> TYPE: DNA
<213> ORGANISM: artificial sequence
<220> FEATURE:
<221> NAME/KEY: misc_feature
<222> LOCATION: ()..()
<223> OTHER INFORMATION: mEmx2 #2 (antisense)

<400> SEQUENCE: 72
ctccggttct gaaaccatac                                              20

<210> SEQ ID NO 73
<211> LENGTH: 21
<212> TYPE: DNA
<213> ORGANISM: artificial sequence
<220> FEATURE:
<221> NAME/KEY: misc_feature
<222> LOCATION: ()..()
<223> OTHER INFORMATION: hEmx2 (sense)

<400> SEQUENCE: 73
cgcccacccc ctaccctcct c                                            21

<210> SEQ ID NO 74
<211> LENGTH: 21
<212> TYPE: DNA
<213> ORGANISM: artificial sequence
<220> FEATURE:
<221> NAME/KEY: misc_feature
<222> LOCATION: ()..()
<223> OTHER INFORMATION: hEmx2 (antisense)

<400> SEQUENCE: 74
accctgtgcc ctcgctgtcc a                                            21

<210> SEQ ID NO 75
<211> LENGTH: 22
<212> TYPE: DNA
<213> ORGANISM: artificial sequence
<220> FEATURE:
<221> NAME/KEY: misc_feature
<222> LOCATION: ()..()
<223> OTHER INFORMATION: SCL (sense)

<400> SEQUENCE: 75
tatgagatgg agatttctga tg                                           22

<210> SEQ ID NO 76
<211> LENGTH: 20
<212> TYPE: DNA
<213> ORGANISM: artificial sequence
<220> FEATURE:
<221> NAME/KEY: misc_feature
<222> LOCATION: ()..()
<223> OTHER INFORMATION: SCL (antisense)
```

```
<400> SEQUENCE: 76
gctcctctgt gtaactgtcc                                               20

<210> SEQ ID NO 77
<211> LENGTH: 20
<212> TYPE: DNA
<213> ORGANISM: artificial sequence
<220> FEATURE:
<221> NAME/KEY: misc_feature
<222> LOCATION: ()..()
<223> OTHER INFORMATION: mBcrp1 (sense)

<400> SEQUENCE: 77
ccatagccac aggccaaagt                                               20

<210> SEQ ID NO 78
<211> LENGTH: 20
<212> TYPE: DNA
<213> ORGANISM: artificial sequence
<220> FEATURE:
<221> NAME/KEY: misc_feature
<222> LOCATION: ()..()
<223> OTHER INFORMATION: mBcrp1 (antisense)

<400> SEQUENCE: 78
gggccacatg attcttccac                                               20

<210> SEQ ID NO 79
<211> LENGTH: 20
<212> TYPE: DNA
<213> ORGANISM: artificial sequence
<220> FEATURE:
<221> NAME/KEY: misc_feature
<222> LOCATION: ()..()
<223> OTHER INFORMATION: CD34 (sense)

<400> SEQUENCE: 79
gggtatctgc ctggaactaa                                               20

<210> SEQ ID NO 80
<211> LENGTH: 19
<212> TYPE: DNA
<213> ORGANISM: artificial sequence
<220> FEATURE:
<221> NAME/KEY: misc_feature
<222> LOCATION: ()..()
<223> OTHER INFORMATION: CD34 (antisense)

<400> SEQUENCE: 80
ttgccaccca accaaatca                                                19

<210> SEQ ID NO 81
<211> LENGTH: 20
<212> TYPE: DNA
<213> ORGANISM: artificial sequence
<220> FEATURE:
<221> NAME/KEY: misc_feature
<222> LOCATION: ()..()
<223> OTHER INFORMATION: CD45 (sense)

<400> SEQUENCE: 81
accatgggtt tgtggctcaa                                               20

<210> SEQ ID NO 82
<211> LENGTH: 20
<212> TYPE: DNA
<213> ORGANISM: artificial sequence
```

```
<220> FEATURE:
<221> NAME/KEY: misc_feature
<222> LOCATION: ()..()
<223> OTHER INFORMATION: CD45 (antisense)

<400> SEQUENCE: 82
gtaatgttcc caaacatggc                                              20

<210> SEQ ID NO 83
<211> LENGTH: 25
<212> TYPE: DNA
<213> ORGANISM: artificial sequence
<220> FEATURE:
<221> NAME/KEY: misc_feature
<222> LOCATION: ()..()
<223> OTHER INFORMATION: Sca-1 (sense)

<400> SEQUENCE: 83
actgtgcctg caaccttgtc tgaga                                        25

<210> SEQ ID NO 84
<211> LENGTH: 20
<212> TYPE: DNA
<213> ORGANISM: artificial sequence
<220> FEATURE:
<221> NAME/KEY: misc_feature
<222> LOCATION: ()..()
<223> OTHER INFORMATION: Sca-1 (antisense)

<400> SEQUENCE: 84
gtccaggtgc tgcctccatt                                              20

<210> SEQ ID NO 85
<211> LENGTH: 30
<212> TYPE: DNA
<213> ORGANISM: artificial sequence
<220> FEATURE:
<221> NAME/KEY: misc_feature
<222> LOCATION: ()..()
<223> OTHER INFORMATION: c-Kit (sense)

<400> SEQUENCE: 85
gaaagaccac agcttaagac tacggtcacg                                   30

<210> SEQ ID NO 86
<211> LENGTH: 26
<212> TYPE: DNA
<213> ORGANISM: artificial sequence
<220> FEATURE:
<221> NAME/KEY: misc_feature
<222> LOCATION: ()..()
<223> OTHER INFORMATION: c-Kit (antisense)

<400> SEQUENCE: 86
atggaattcc ttatgatcac aaatgg                                       26
```

METHOD OF PURIFICATION OF CELLS

FIELD OF THE INVENTION

The present invention relates generally to a method for the generation of a substantially homogeneous population of undifferentiated cells. More particularly, the present invention relates to the purification of a substantially homogeneous population of stem cells and their progenitor or precursor cells. Even more particularly, the present invention provides a population of neural stem cells (NSCs). The subject invention is particularly directed to NSCs and precursor cells with the capacity to differentiate into cells and cell lineages required for the development maintenance or repair of the central nervous system in an animal such as a mammal. The present invention is further directed to NSCs and progenitor and/or precursor cells which are capable of proliferation and differentiation into multiple cell lineages, such as but not limited to neurons, oligodendrocytes, glia and astrocytes. The subject invention further contemplates the use of NSCs and/or precursor cells for the repair or regeneration of tissue, such as tissue associated with the central nervous system, in an animal including a mammal. The NSCs of the present invention may be used to identify naturally occurring molecules such as cytokines as well as molecules obtained from natural product screening or screening of chemical libraries which induce proliferation of the NSCs. Such molecules are useful in the development of therapeutics.

BACKGROUND OF THE INVENTION

Reference to any prior art in this specification is not, and should not be taken as, an acknowledgment or any form of suggestion that this prior art forms part of the common general knowledge in any country.

Stem cells are undifferentiated cells which are capable of proliferation and, self-maintenance, have the ability and capacity to generate a large repertoire of functional, differentiated progeny and are capable of responding to stimuli to initiate a regeneration of tissue after an injury. During embrogenesis, and after birth, stem cells are present in tissues which have high turnover of terminally differentiated cells such as blood and skin cells. Stem cells are also found to exist in tissues with little turnover of differentiated cells. An example mammalian tissue exhibiting low turnover is the adult mammalian central nervous system or central nervous system (CNS) [Reynolds, B. A. and Weiss, S., *Science* 255: 1707-1710, 1992; Richards et al., *Natl. Acad. Sci. USA* 89: 8591-8595, 1992; McKay, R., *Science* 276: 66-71, 1997; Gage, F. H., *Science* 287: 1433-1438, 2000].

The putative role of stem cells in the adult animal or human is to replace cells which are lost by natural cell death, injury or disease. To date, treatment for replacing defective or damaged organs or tissues has primarily been achieved via allogenic transplantation and by the administration of pharmaceutical compounds to reduce an immune response which can arise when allographed material is incompatible with the recipient. Recently, the concept of tissue grafting has been applied to the treatment of numerous diseases. In allografting procedures, either whole organs may be replaced or transplanted or small sections of tissue replaced such as in a skin graft. More recently, multipotent stem cells have been proposed for use in allograft procedures. In this type of allograft strategy, stem cells which have the capacity to differentiate into a particular tissue type are transplanted into a recipient. Generally, stem cells then receive signals from surrounding tissue or other forms of stimulus resulting ultimately in differentiation into a mature cell. In such procedures, it is necessary to isolate stem cells with the potential to develop along a particular pathway and into a desired mature cell. In order to achieve this it is necessary to isolate a quantity of stem cells. Generally, large numbers of stem cells are required. Suitable sources of sufficient numbers of stem cells can be harvested from embryonic and/or adult sources. However, current protocols for the culture of stem cells are cumbersome and often cannot provide sufficient numbers of stem cells required for tissue replacement therapy. In fact, hemopoietic stem cells cannot be expanded in culture. NSCs, however, do have the capacity to be expanded in culture but, until the advent of the present invention, it was not possible to initiate the culture with a homogenous population of NSCs. Thus, the development of stem cell tissue replacement therapy will require an ability to isolate and culture appropriate quantities of stem cells that will differentiate along a known pathway.

The fertilized egg is the ultimate stem cell from which all other cell lineages derive. As development proceeds, early embryonic cells respond to growth and differentiation signals which gradually narrow the cell's developmental potential, until the cells reach developmental maturity, and become terminally differentiated. These terminally differentiated cells have specialized functions and characteristics, and represent the last step in a multi-step process of precursor cell differentiation into a particular cell. The transition from one step to the next in cell differentiation is governed by specific biochemical mechanisms that gradually control the progression of cell differentiation until maturity is reached. It is clear that differentiation of tissues and cells is a gradual process that follows specific steps until a terminally differentiated state is reached. Thus, stem cells represent a source of undifferentiated cells which can be used in the maintenance of tissues whether during normal life or in response to injury and disease.

An expanded pool of stem and progenitor cells, as well as non-terminally differentiated cells that could supply a desired differentiation phenotype would be of great value in therapies that involve tissue replacement. To allow cell replacement therapy to become widely applicable in the clinical domain, a considerable challenge is to address the problem of provision of suitable quantities of replenishing stem cells that are capable of differentiating into a particular cell type.

During development of the CNS, multipotent precursor cells, i.e. NSCs, proliferate, giving rise to transiently dividing progenitor cells that eventually differentiate into the cell types that compose the adult brain. Some NSCs have also been shown to possess the potential to give rise to hemopoietic and muscle cells (Clark, D. L., *Science* 288: 1660-1663, 2000; Bjornson et al., *Science* 283: 534-537, 1999). NSCs are classically defined as having the ability to self-renew, to proliferate and been shown to differentiate into multiple different phenotypic lineages including neurons, astrocytes and oligodendrocytes. NSC activity has been detected from all mammalian species studied to date including mice, rats, non-human primates and humans.

Although methods for obtaining and culturing multipotent NSCs have been previously described, a major problem with the resulting population of cells is that they provide very low percentages of NSCs. Importantly, the populations of cells obtained are mixed and contain other cell types. Such cell populations would need to undergo complicated enrichment to increase the proportion of NSCs if used for transplantation procedures. Such cultivation procedures, however, do not address the presence of heterogeneity in the mixed cells in the populations which have diverse differentiation characteristics. Typically, less that 0.1% of cells obtained from neural tissue are multipotent stem cells. Thus, there is a clear need for a method which permits the purification of these multipotent stem cells to homogeneity.

In work leading up to the present invention, the inventors sought to provide a method for the isolation of a substantially homogenous population of undifferentiated cells and in particular stem cells and more particularly NSCs. The inventors utilized cell surface markers in combination with cell sorting procedures based on cell size to purify a population of NSCs to substantial homogeneity. Surprisingly, the inventors determined that a highly homogenous population of NSCs can be isolated from mammalian brain tissue. Furthermore, the inventors have developed protocols and methods to propagate NSCs and form a highly homogenous population of NSCs which retain the ability to differentiate into mature cell lineages. Thus, the instant invention overcomes the difficulty of producing undifferentiated cells in purified form. The homogeneous cell populations of the present invention are useful in a range of situations including transplantation methodologies in therapeutic approaches to repair and replace damaged and/or dysfunctional tissue, tissue augmentation, delivery of genetic and proteinaceous molecules including therapeutic cytokine delivery, identification of factors controlling differentiation and/or proliferation including inhibitors thereof and identification of diagnostic and therapeutic markers. Furthermore, by identifying and purifying, a NSC population, it can be determined which factor(s) regulate the proliferation, self-maintenance and differentiative properties of NSCs in situ, thereby overcoming the need for transplantation of donor cells. The activation of NSCs in situ represents a major advantage over transplantation therapies in that it avoids major surgery and issues of tissue rejection.

SUMMARY OF THE INVENTION

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Nucleotide and amino acid sequences are referred to by a sequence identifier number (SEQ ID NO:). The SEQ ID NOs: correspond numerically to the sequence identifiers <400>1 (SEQ ID NO: 1), <400>2 (SEQ ID NO:2), etc. A sequence listing is provided after the claims.

The present invention relates to the purification of a substantially homogeneous population of undifferentiated cells such as stem cells which are capable of differentiation into multiple mature cell lineages. In particular, the present invention provides NSCs that may be used in transplantation strategies for the replacement or repair of degenerate tissue. The ability to now generate homogenous populations of stem cells further enables the identification of factors which may be used to stimulate proliferation, differentiation and self-maintenance of stem cells in vivo. The present invention is particularly directed to NSCs and neural progenitor and precursor cells with the capacity to differentiate into cells and cell lineages required for the development, maintenance, or repair of tissue associated with a central nervous system in animals, mammals and humans. The present invention further provides methods for the purification of NSCs which are capable of proliferation and differentiation into distinct functional progeny which constitutes the functional cells of the CNS. Cell types that can be derived from the NSCs of the present invention include but are not limited to neurones, oligodendrocytes, glia and astrocytes. Cell types also include bone marrow cells amongst other non-neural cells. The subject invention further contemplates the use of NSCs for the repair or regeneration of tissue associated with the CNS, as well as in tissue augmentation, gene therapy and therapeutic drug targeting in an animal or a human. The NSCs of the present invention and their progenitors or precursors are further useful in a method for repair and/or regeneration of tissue in an animal or a mammal such as a human. The instant invention is further useful in transplantation and differentiation of NSCs in an animal or a mammal such as a human. The present invention provides a method for the prophylaxis and treatment of neuro-degenerative disorders and to correct neurological dysfunction and/or trauma. Furthermore, the NSC cultures prepared in accordance with the present invention are useful in screening for molecules which can influence the growth and differentiation of stem cells. Such molecules are referred to as endogenous activators. The use of endogenous activators avoids the need for transplantation of stem cells into a subject.

The present invention is predicated in part, therefore, on the development of a method for generating a substantially homogeneous population of undifferentiated cells. Undifferentiated cells include primordial cells insatiable from neural tissue which are capable of differentiation and proliferation into multiple cell lineages and capable of self-renewal.

Accordingly, the present invention contemplates a method for generating a substantially homogeneous population of undifferentiated cells from a biological sample, said method comprising subjecting said biological sample or a sub-sample thereof to tissue-disruption means to provide a mixed population comprising the undifferentiated cells to be purified, subjecting said mixed population of cells to cell size-discrimination means to generate a population of cells wherein substantially all cells fall within a particular size range and simultaneously or sequentially with the size-discrimination step, subjecting said population to cell surface marker-discrimination means to generate a substantially homogeneous population of undifferentiated cells.

More particularly, the present invention provides a method for generating a substantially homogeneous population of pluripotent NSCs from a biological sample, said method comprising subjecting said biological sample or a sub-sample thereof to tissue-disruption means to provide a mixed population comprising the NSCs to be purified, subjecting said mixed population of cells to cell size-discrimination means to generate a population of cells wherein substantially all cells fall within a particular size range and simultaneously or sequentially with the size-discrimination step, subjecting said population to cell surface marker-discrimination means to generate a substantially homogeneous population of undifferentiated cells.

Another aspect of the present invention uses cell surface and internal protein and nucleic acid markers to characterize and/or select particular populations of cells which may or may not comprise NSCs. In essence, three populations of cells are characterized based on the level of heat stable antigen (HSA) and peanut agglutinin (PNA). A population having low levels of HSA and PNA (i.e. $HSA^{lo}$ $PNA^{lo}$) comprises essentially all NSCs; a population comprising level levels of HSA and low levels of PNA (i.e. $HSA^{hi}$ $PNA^{lo}$) comprises some progenitor cells; a population of phenotypically $HSA^{lo}$ $PNA^{hi}$ or $HSA^{hi}$ $PNA^{hi}$ comprises differentiated cells.

The substantially homogenous NSC population (i.e. phenotypically $HSA^{lo}$ $PNA^{lo}$) may be further characterized as lacking EphA4, TrkA, TrkC, LIFRβ, ζ1, SOCS2, SOCS3, Pax6, Tbr1, Plx2, SCL, Bcrp1 and Sca-1; having reduced levels of p75 and Trbβ; and expressing DCC, neogenin, Notch 1, 2 and 3, Dlx1 and Sox2.

Other useful HSA$^{lo}$ PNA$^{lo}$ markers which are at low levels of cells phenotypically HSA$^{lo}$ PNA$^{lo}$ include CD3e, CD4, CD8a, CD11b, CD19, CD24 (equivalent to HSA), mCD30.1, CD1, CD34, CD41, CD45R, CD45RA, CD45RB, CD45RC, CD45RO, CD89, CD90.2, CD99R, CD117, CD135, H-2K$^b$ and Sca-1.

The present invention identifies NSCs which are destined to become neural cells such as neurons. The present invention extends, therefore, to any drug or naturally or non-naturally occurring molecules which act on the subject NSCs to facilitate proliferation and/or differentiation into particular neural cells.

BRIEF DESCRIPTION OF THE FIGURES

FIG. 1A is a graphical representation of a dot plot showing the FACS sorting of viable cells by forward light scatter (<7 μm, 7-12 μm and >12 μm) and PNA expression (PNA$^{lo}$ box, PNA$^{mid}$ and PNA$^{hi}$ box).

FIG. 1B is a graphical representation of a dot plot showing FACS sorting of viable cells (which are >12 μm or 90 units) by PNA expression and HSA expression. Gated region indicates PSA$^{lo}$ HSA$^{lo}$ cells.

FIG. 1C is a graphical representation showing a FACS contour plot of the PSA$^{lo}$ HSA$^{lo}$ cells of the gated region shown in FIG. 1B.

Figure 2A:
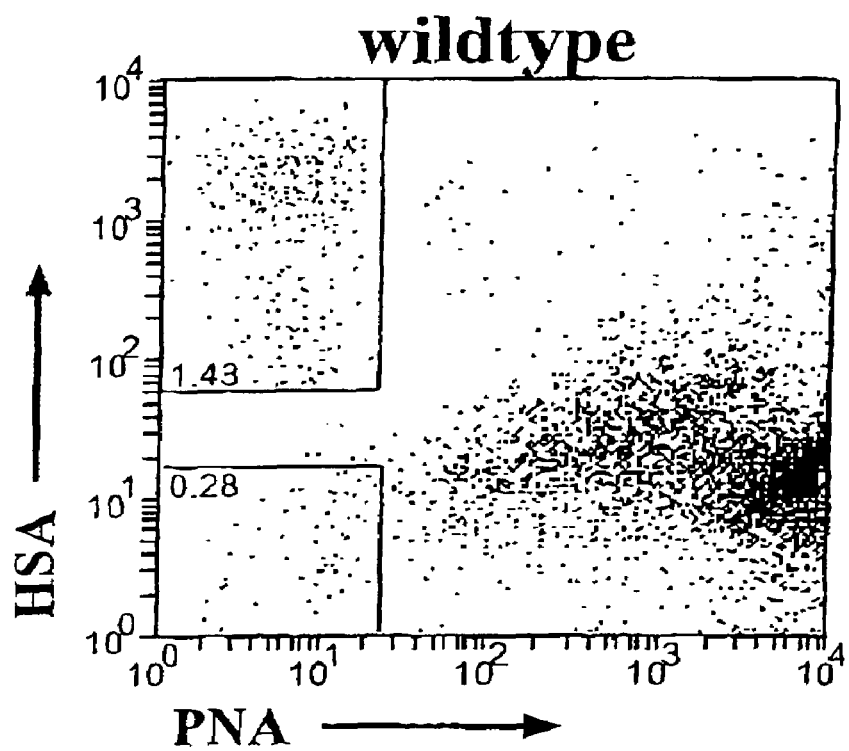
FIG. 2A is a graphical representation of a dot plot showing FACS sorting of viable cells (which are >12 μm or 90 units) by PNA expression and HSA expression. These cells have been harvested form an individual wild-type littermate control mouse as compared to a querkopf mutant mouse which was employed in FIG. 2B. Values within gated regions indicates the percentage of cells contained within that region, as compared to overall viable cell number. For example, PNA$^{lo}$ HSA$^{lo}$ cells represent 0.28% while PNA$^{lo}$ HSA$^{mid-hi}$ cells represent 1.43% of overall viable cells.

A list of abbreviations used in the subject specification is provided in Table 1

TABLE 1

| ABBREVIATION | DEFINITION |
|---|---|
| C2C12 | myoblast cell line fast-fusing sub-clone of the C2 cell line |
| DAPI | 4',6-diamidino-2-phenylindole, dihydrochloride |
| FACS | Fluorescent Activated Cell Sorting |
| GFP | green fluorescent protein |
| HSA | heat stable antigen (mCD24a) |
| HSA$^{lo}$ | a NSC with low or absent HSA surface antigen |
| HSCs | haemopoetic stem cells |
| NSCs | neural stem cells |
| PNA | pcanut agglutinin |
| PNA$^{lo}$ | a neural stem cell with low or absent PNA surface antigen |
| MyHC | myosin heavy chain |
| TRITC | traditional rhodamine isothiocyanate |
| FITC | fluoro isothiocyanate |
| PNA$^{hi}$ | a NSC with high levels of PNA surface antigen |
| HSA$^{hi}$ | a NSC with high levels of HSA surface antigen |

A summary of sequence identifiers used throughout the subject specification is provided in Table 2.

TABLE 2

| SEQUENCE ID NO: | DESCRIPTION |
|---|---|
| 1 | 5'→ 3' sense mβ-actin primer |
| 2 | 5'→ 3' antisense mβ-actin primer |
| 3 | 5'→ 3' sense hβ-actin primer |
| 4 | 5'→ 3' antisense hβ-actin primer |
| 5 | 5'→ 3' sense mEphA4 primer |
| 6 | 5'→ 3' antisense mEphA4 primer |
| 7 | 5'→ 3' mDCC primer |
| 8 | 5'→ 3' antisense mDCC primer |
| 9 | 5'→ 3' sense mRyk primer |
| 10 | 5'→ 3' antisense mRyk primer |
| 11 | 5'→ 3' sense mNeogenin splice #1 primer |
| 12 | 5'→ 3' antisense mNeogenin splice #1 primer |
| 13 | 5'→ 3' sense mNeogenin splice #2 primer |
| 14 | 5'→ 3' antisense mNeogenin splice #2 primer |
| 15 | 5'→ 3' sense mNeogenin splice #4 primer |
| 16 | 5'→ 3' antisense mNeogenin splice #4 primer |
| 17 | 5'→ 3' sense mTrkA primer |
| 18 | 5'→ 3' antisense mTRrkA primer |
| 19 | 5'→ 3' sense mTrkB primer |
| 20 | 5'→ 3' antisense mTrkB primer |
| 21 | 5'→ 3' sense mTrkC primer |
| 22 | 5'→ 3' antisense mTrkC primer |
| 23 | 5'→ 3' sense mp75 primer |
| 24 | 5'→ 3' antisense mp75 primer |
| 24 | 5'→ 3' antisense mp75 primer |
| 25 | 5'→ 3' sense mLIFRβ primer |

TABLE 2-continued

| SEQUENCE ID NO: | DESCRIPTION |
|---|---|
| 26 | 5'→ 3' antisense mLIFβ primer |
| 27 | 5'→ 3' sense mgp130 primer |
| 28 | 5'→ 3' antisense mgp130 primer |
| 29 | 5'→ 3' sense mNR6 primer |
| 30 | 5'→ 3' antisense mNR6 primer |
| 31 | 5'→ 3' sense mNotch 1 primer |
| 32 | 5'→ 3' antisense mNotch 1 primer |
| 33 | 5'→ 3' sense mNotch 2 primer |
| 34 | 5'→ 3' antisense mNotch 2 primer |
| 35 | 5'→ 3' sense mNotch 3 primer |
| 36 | 5'→ 3' antisense mNotch 3 primer |
| 37 | 5'→ 3' sense mζ1 primer |
| 38 | 5'→ 3' antisense mζ1 primer |
| 39 | 5'→ 3' sense mSOCS1 primer |
| 40 | 5'→ 3' antisense mSOCS1 primer |
| 41 | 5'→ 3' sense SOCS2 primer |
| 42 | 5'→ 3' antisense SOCS2 primer |
| 43 | 5'→ 3' sense SOCS3 primer |
| 44 | 5'→ 3' antisense SOCS3 primer |
| 45 | 5'→ 3' sense mPax6 primer |
| 46 | 5'→ 3' antisense mPax6 primer |
| 47 | 5'→ 3' sense hPax primer |
| 48 | 5'→ 3' antisense hPax primer |
| 49 | 5'→ 3' sense mTbr1 primer |
| 50 | 5'→ 3' antisense mTbr1 primer |
| 51 | 5'→ 3' sense hTbr 1 primer |
| 52 | 5'→ 3' antisense hTbr 1 primer |
| 53 | 5'→ 3' sense mSvet 1 primer |
| 54 | 5'→ 3' antisense mSvet 1 primer |
| 55 | 5'→ 3' sense mNkx2.1 primer |
| 56 | 5'→ 3' antisense mNkx2.1 primer |
| 57 | 5'→ 3' sense mDlx1 primer |
| 58 | 5'→ 3' antisense mDlx1 primer |
| 59 | 5'→ 3' sense mDlx2 primer |
| 60 | 5'→ 3' antisense mDlx2 primer |
| 61 | 5'→ 3' sense mSox1 primer |
| 62 | 5'→ 3' antisense mSox1 primer |
| 63 | 5'→ 3' sense mSox2 primer |
| 64 | 5'→ 3' antisense mSox2 primer |
| 65 | 5'→ 3' sense mEmx1 primer |
| 66 | 5'→ 3' antisense mEmx1 primer |
| 67 | 5'→ 3' sense hEmx1 primer |
| 68 | 5'→ 3' antisense hExm1 primer |
| 69 | 5'→ 3' sense mEmx2 #1 primer |
| 70 | 5'→ 3' antisense mEmx2 #1 primer |
| 71 | 5'→ 3' sense mEmx2 #2 primer |
| 72 | 5'→ 3' antisense mEmx2 #2 primer |
| 73 | 5'→ 3' sense hExm2 primer |
| 74 | 5'→ 3' antisense hExm2 primer |
| 75 | 5'→ 3' sense SCL primer |
| 76 | 5'→ 3' antisense SCL primer |
| 77 | 5'→ 3' sense mBcrp1 primer |
| 78 | 5'→ 3' antisense mBcrp1 primer |
| 79 | 5'→ 3' sense CD34 primer |
| 80 | 5'→ 3' antisense CD34 primer |
| 81 | 5'→ 3' sense CD45 primer |
| 82 | 5'→ 3' antisense CD45 primer |
| 83 | 5'→ 3' sense Sca-1 primer |
| 84 | 5'→ 3' antisense Sca-1 primer |
| 85 | 5'→ 3' sense c-Kit primer |
| 86 | 5'→ 3' antisense c-Kit primer |

DETAILED DESCRIPTION OF THE PREFERRED EMBODIMENTS

The present invention is predicated in part on the development of a method for generating a substantially homogeneous population of undifferentiated cells. Undifferentiated cells include an oligopotent or pluripotent cell capable of differentiation and proliferation into multiple cell types or lineages as well as self-renewal. Preferred undifferentiated cells are NSCs.

The present invention further contemplates the use of NSCs and their progeny in a method for repair, regeneration and/or augmentation of tissue in an animal or a mammal such as a human. Such an approach includes delaying cellular degeneration and senescence. The instant invention is further directed to the transplantation and differentiation of NSCs in an animal or a mammal such as a human for the prophylaxis and treatment of neuro-degenerative disorders and to correct neurological dysfunction and/or trauma. The ability to generate a purified preparation of stem cells or their precursors enables the screening of molecules and compounds and genetic elements which influence or otherwise facilitate cell proliferation and/or differentiation. In particular, the present invention provides for the use of purified stem cells to screen for molecules capable of influencing the growth, proliferation and/or differentiation of stem cells. Such molecules enable proliferation and differentiation of endogenous stem cells thereby avoiding the need to proliferate cells in culture and transplanting them to a subject. Furthermore, purified stem cells permit the identification of cell surface markers capable of interaction with ligands including antibodies. Such markers are useful in monitoring stein cells and/or the efficacy of therapeutic protocols. Importantly, the present invention identifies the population of NSCs which are destined to become neuronal cells. Accordingly, the present invention extends to any drugs or agents which act on these cells to facilitate proliferation and/or further differentiation.

Reference herein to a "population" of cells means two or more cells. A "homogeneous populations" means a population comprising substantially only one cell type. A "cell type" may be cells of the same lineage or sub-type having substantially the same physiological status.

Accordingly, the present invention contemplates a method for generating a substantially homogeneous population of undifferentiated cells from a biological sample, said method comprising subjecting said biological sample or a sub-sample thereof to tissue-disruption means to provide a mixed population comprising the indifferentiated cells to be purified, subjecting said mixed population of cells to cell size-discrimination means to generate a population of cells wherein substantially all cells fall within a particular size range and simultaneously or sequentially with the size-discrimination step, subjecting said population to cell surface marker-discrimination means to generate a substantially homogeneous population of undifferentiated cells.

Preferably, the undifferentiated cells are neural stem cells (NSCs).

Reference herein to a "substantially homogeneous population" refers to a cell population in which a substantial number of the total population of the cells are of the same type and/or are in the same state of differentiation. Preferably, a "substantially homogeneous population" of undifferentiated cells comprises a population of cells of which least about 50% are of the same cell type, more preferably that at least 75% are of the same cell type even more preferably 85% are of the same cell type, still even more preferably at least 95% of the cells are the same type, and even more preferably 97% (e.g. 98%, 99% or 100%) are of the same cell type.

The term "tissue-disruption means" includes dissociation of individual cells from the connecting extracellular matrix (ECM) of the tissue. Preferably, a single cell suspension is produced. Preferably, the individual cells are of a minimal size such as from about 5 to about 50 microns or from about 7 to about 30 microns or from about 7 to about 20 microns. Most preferably, the cells are greater than about 12 microns.

"Undifferentiated" means a primordial state of a cell or cells capable of differentiation and proliferation to produce progeny cells that can be physiologically, biochemically, morphologically, anatomically, immunologically, physiologically, or genetically distinct from the primordial state.

As stated above, the preferred undifferentiated cells are stem cells and are more preferably NSCs which can give rise to multiple cell lineages, are capable of differentiation and proliferation and are capable of self-renewal. The most preferred NSCs give rise to neuronal cells. The NSCs may be pluripotent NSCs or non-pluripotent NSCs or a mixture of both.

A "biological sample" is a tissue or organ such as but not limited to epithelial tissue, liver tissue, muscle tissue, adipose tissue, connective tissue, bone marrow, blood or nervous tissue. A "sub-sample" may a portion of a tissue, such as a biopsy or a part or portion of an organ or a tissue. An in vitro culture of cells is also regarded as a biological sample.

In another embodiment of the present invention, there is provided a substantially homogeneous population of undifferentiated cells prepared by the method of comprising subjecting a biological sample or a sub-sample thereof to tissue-disrupting means to provide a mixed population comprising the undifferentiated cells, subjecting said mixed population of cells to cell size-discrimination means to generate a population of cells wherein substantially all cells fall within a particular size range and simultaneously or sequentially with the size-discrimination step, subjecting said population to undifferentiated cell surface marker-discrimination means to generate a substantially homogeneous population of undifferentiated cells.

The term "comprising" as used above and elsewhere in the subject specification means that the mixed population of cells includes undifferentiated cells amongst other potential cell types.

By sequential and/or simultaneous is meant at the same time (i.e. simultaneous) or within microseconds, seconds, minutes, hours or days (i.e. sequential). Accordingly, size-discrimination and cell surface marker discrimination may be conducted at the same time or within seconds, minutes, hours or days of each other.

In another embodiment of the present invention, there is provided a substantially homogeneous population of NCSs prepared by the method comprising subjecting a biological sample or a sub-sample thereof to tissue-disrupting means to provide a mixed population comprising the NSCs, subjecting said mixed population of cells to cell size-discrimination means to generate a population of cells wherein substantially all cells fall within a particular size range and simultaneously or sequentially with the size-discrimination step, subjecting said population to stem cell surface marker-discrimination means to generate a substantially homogeneous population of NSCs.

The present invention provides, therefore, a method of producing a homogenous population of NSCs which are capable of giving rise to multiple cell lineages. This provides a means for gene therapy, augmentation therapy and therapy to repair, replace and to delay senescence neural and non-neural tissue. It also enables identification of growth factors and other agents which can promote proliferation and/or differentiation of endogenous cells.

The present invention provides, therefore, in one embodiment, a method for cell replacement therapy in an animal, said method comprising, generating a substantially homogeneous population of NSCs from a biological sample, said method comprising subjecting said biological sample or a sub-sample thereof to tissue-disrupting means to provide a mixed population comprising the NSCs, subjecting said mixed population of cells to cell size-discrimination means to generate a population of NSCs wherein substantially all cells fall within a particular size range and simultaneously or sequentially with the size-discrimination step, subjecting said population to cell surface marker discrimination means to generate a substantially homogeneous population of NSCs and then introducing said homogeneous population of cells to said same animal or an animal capable of receiving said NSCs.

Reference herein to "cell replacement therapy" includes, in one form, a process in which undifferentiated cells are strategically placed in vivo or in vitro such as to differentiate and proliferate into a particular cell lineage or into multiple cell lineages. Thus, cell replacement therapy requires that an undifferentiated cell appropriately differentiates for the purposes of providing repair, regeneration or replacement of a cell function including the replacement of an organ or a tissue. "Cell replacement therapy" also includes augmentation therapy. The latter includes the removal of existing cells or tissue, expanding in culture and then replacing. This is a particular advantage of the present invention where a single or a few NSCs are capable of expansion in culture to a large number of NSCs. This is not a feature of hemopoietic stem cells which cannot be expanded in a culture. The subject into which the purified stem cells or their progeny are implanted for the purpose of "cell replacement therapy" or repair of tissue, or from which stem cells can be derived, is preferably an animal including but not limited to animals such as cows, pigs, horses, chickens, cats, docs and is preferably a mammal such as a primate and most preferably a human.

By "tissue" is meant a part of an organism consisting of a number of cells having a similar structure or a similar function. For example, neural tissue may consist of a number of cells comprising one or more cell type including but not limited to neurones, glia, oligodendrocytes, astrocytes and ependymal cells. Organs are considered herein to comprise tissue and a brain is encompassed by the term organ, and a sub-sample includes a biopsy of a tissue such as but not limited to nervous tissue or an organ such as but not limited to a brain.

Reference herein to an "animal" refers to mammal, reptile, amphibian, fish or bird or a live stock animal. More preferably, the animal is a mammal such as a human or a primate.

The present invention provides composition for cell replacement therapy wherein the composition comprises a substantially homogeneous population of NSCs.

The NSCs may be pluripotent or oligopotent or may be committed to neuronal cell development or be a mixture of two or more of the above.

In this embodiment, the present invention provides a composition for use in cell replacement therapy, said composition comprising a population of substantially homogeneous NSCs prepared by the method of generating a substantially homogeneous population of NSCs from a biological sample, said method comprising subjecting said biological sample or a sub-sample thereof to tissue-disrupting means to provide a mixed population comprising the NSCs, subjecting said mixed population of cells to cell size-discrimination means to generate a population of cells wherein substantially all cells fall within a particular size range and simultaneously or sequentially with the size-discrimination step, subjecting said population to undifferentiated cell surface marker discrimination means to generate a substantially homogeneous population of NSCs.

The present invention is directed to methods of the purification of non-terminally differentiated cells or undifferentiated cells, such that the differentiation of the cell is not inhibited without destroying the ability of the cell to proliferate. As used herein, "pluripotent cells" shall mean any non-terminally differentiated cells. The undifferentiated cell is preferably an NSC.

A "stem cell" is an undifferentiated cell that can be induced to proliferate and generate progeny which includes but is not limited to more stem cells or more differentiated progeny or more mature cell types, while also retaining one or more cells with parental developmental potential. In other words, a stem cell is a pluripotent cell capable of self-renewal and differentiation into multiple cell lineages. In many biological instances, stem cells are also considered to be pluripotent because they can produce progeny of more than one distinct tissue type. The ability of a stem cell to self-renew itself is an essential aspect of the definition of a stem cell as used herein. Stem cells may divide asymmetrically, with one daughter retaining the stem cell state and the other daughter expressing a specific function and/or a phenotype distinct from the first mentioned daughter cell. Alternatively, some of the stem cells in a population cain divide symmetrically into two stem cells, thus maintaining the same stem cells in the population as a whole, while other cells in the population give rise to differentiated progeny only. It is possible that cells that begin as stem cells might proceed towards a differentiated phenotype, but then reverse and re-express a stem cell phenotype. A stem cell is an operational term meaning a cell which can divide to produce another stem cell (i.e. has a self renewal capacity), as well as a cell which can differentiate along multiple specific differentiation paths. It is often the case that a particular cell with a differentiation lineage has derived from a less differentiated parent and can still divide and give rise to a more differentiated cellular progeny. In a preferred embodiment of the present invention the population of undifferentiated cells are stem cells, and more preferably are pluripotent NSCs.

The NSCs in the homogeneous population of the present invention are in a viable state and, hence, have potential in various therapeutic protocols especially in the treatment of CNS disorders.

CNS disorders encompass numerous afflictions such as neurodegenerative diseases (e.g. Alzheimer's disease and Parkinson's disease), acute brain injury (e.g. stroke, head injury, cerebral palsy) and a large number of CNS dysfunctions (e.g. depression, epilepsy, and schizophrenia). In recent years, neurodegenerative disease has become an important concern due to the expanding elderly population which is at greatest risk for these disorders. These diseases, which include Alzheimer's disease, multiple sclerosis (MS), Huntington's disease, amyotrophic lateral sclerosis and Parkinson's disease, have been linked to the degeneration of neural cells in particular locations of the CNS, leading to the inability of these cells or the brain region to carry out their intended function. Degeneration in a brain region known as the basal ganglia can lead to diseases with various cognitive and motor symptoms, depending on the exact location. The basal ganglia consists of many separate regions, including the striatum (which consists of the caudate and putamen), the globus pallidus, the substantia nigra, substantia innomiate, ventral pallidum, nucleus basalis of Meynert, ventral tegmental area and the subthalamic nucleus. Preferably, differentiation of NSCs can replace damaged neural and/or non-neural tissue. Preferably, the pluripotent NSCs are used in cell replacement therapy, tissue augmentation therapy, gene therapy, amongst other methodologies. Alternatively, growth factors, identified using purified cultures of NSCs, are used to stimulate NSC proliferation and/or differentiation of cells in vivo.

The present invention provides, therefore, in one embodiment, a method for the replacement of neural or non-neural tissue in an animal, said method comprising, generating a substantially homogeneous population of NSCs from a biological sample, said method comprising subjecting said biological sample or a sub-sample thereof to tissue-disrupting means to provide a mixed population comprising said cells, subjecting said mixed population of the cells to cell size-discrimination means to generate a population of cells wherein substantially all cells fall within a particular size range and simultaneously or sequentially with the size-discrimination step, subjecting said population to cell surface marker discrimination means to generate a substantially homogeneous population of NSCs and then introducing said homogeneous population of said cells to said same animal or an animal capable of receiving said cells.

The term "animal" includes a human, primate, livestock animal, laboratory test animal, avian species and fish species, amongst other animals.

In a particular embodiment, the present invention provides a composition for use in nerve tissue replacement therapy, said composition comprising a population of substantially homogeneous NSCs prepared by the method of generating a substantially homogeneous population of NSCs from a biological sample, said method comprising subjecting said biological sample or a sub-sample thereof to tissue-disrupting means to provide a mixed population comprising said cells, subjecting said mixed population of the cells to cell size-discrimination means to generate a population of cells wherein substantially all cells fall within a particular size range and simultaneously or sequentially with the size-discrimination step, subjecting said population to cell surface marker discrimination means to generate a substantially homogeneous population of NSCs.

A number of cell isolation, cell separation and cell purging strategies are known for purifying or removing cells from a suspension comprising a diverse population of cells. Cell separation methods are used to isolate cells or purge cell suspensions or cell populations typically fall into one of three broad categories. Physical separation methods typically exploit differences in a physical property between cell types, such as cell size or density (e.g. centrifugation or elutriation); chemical-based methods typically employ an agent which selectively kills or purges one or more undesirable cell types; and affinity-based methods typically exploit antibodies or molecules with a selective binding capacity which bind selectively to marker ligands on a cell membrane surface of desired or undesired cell types, which antibodies may subsequently enable the cells to be isolated or removed from the suspension. It is not intended that the method of purification of cells of NSCs be limited to any one method, however, methods of physical separation are advantageous with regard to their ability to separate cells of a particular dimension, without causing undue damage to the desired cells. In this regard, it is preferable that the substantially homogeneous population of NSCs are subjected to size discrimination means, such that the substantially homogeneous population of undifferentiated cells comprises NSCs that are about 12 microns or greater in diameter.

Accordingly, the present invention contemplates a method for generating a substantially homogeneous population of undifferentiated cells that are greater than about 12 microns in diameter from a biological sample, said method comprising subjecting said biological sample or a sub-sample thereof to tissue-disruption means to provide a mixed population comprising the cells to be purified, subjecting said mixed population of cells to cell size-discrimination means to generate a population of cells wherein substantially all cells are from about 5 to about 50 microns in diameter and simultaneously or sequentially with the size-discrimination step, subjecting said population to undifferentiated cell surface marker-discrimination means to generate a substantially homogeneous population of undifferentiated cells that are from about 5 to about 50 microns in diameter.

Preferably, the population of undifferentiated cells comprises stem cells and even more preferably, they are NSCs.

In a preferred embodiment of the present invention, therefore, there is provided a substantially homogeneous population of NSCs which are from about 5 to about 50 microns in diameter prepared by the method of comprising subjecting a biological sample or a sub-sample thereof to tissue-disrupting means to provide a mixed population comprising the NSCs, subjecting said mixed population of cells to cell size-discrimination means to generate a population of cells wherein substantially all cells are from about 5 to about 50 microns in diameter and simultaneously or sequentially with the size-discrimination step, subjecting said population to NSCs surface marker-discrimination means to generate a substantially homogeneous population of NSCs which are from about 5 to about 50 microns in diameter.

It is preferable that the population of NSCs used to replace or repair neural tissue are from about 5 to about 50 microns in diameter.

The present invention provides, therefore, a method for the replacement of neural tissue in an animal, said method comprising, generating a substantially homogeneous population of NSCs which are from about 5 to about 50 microns in diameter from a biological sample, said method comprising subjecting, said biological sample or a sub-sample thereof to tissue-disrupting means to provide a minced population comprising NSCs, subjecting said mixed population of cells to cell size-discrimination means to generate a population of cells wherein substantially all cells are from about 5 to about 50 microns in diameter and simultaneously or sequentially with the size-discrimination step, subjecting said population to cell surface marker discrimination means to generate a substantially homogeneous population of NSCs which are from about 5 to about 50 microns in diameter and then introducing said homogeneous population of NSCs which are from about 5 to about 50 microns in diameter to said same animal or an animal capable of receiving said NSCs.

Preferably, the composition of the present invention comprise NSCs which are from about 5 to about 50 microns in diameter that are capable of proliferation and/or differentiating into neural tissue.

In this embodiment, the present invention provides a composition for use in nerve tissue replacement therapy, said composition comprising a population of substantially homogeneous NSCs which are from about 5 to about 50 microns in diameter prepared by the method of generating a substantially homogeneous population of NSCs which are from about 5 to about 50 microns in diameter from a biological sample, said method comprising subjecting said biological sample or a sub-sample thereof to tissue-disrupting means to provide a mixed population comprising NSCs, subjecting said mixed population of cells to cell size-discrimination means to generate a population of cells wherein substantially all cells are from about 5 to about 50 microns in diameter and simultaneously or sequentially with the size-discrimination step, subjecting said population to cell surface marker discrimination means to generate a substantially homogeneous population of NSCs.

Reference herein to "about" refers to a value of +/− 3 microns. Preferably, the cell size is from about 7 to about 30 and even more preferably from about 7 to about 20 microns. Generally, a size of greater than about 12 microns is particularly useful.

In instances where the goal of the separation of a mixed population of nerve cells is to produce a substantially homogeneous population of NSCs, antibodies and cell specific surface markers which present on NSCs can be used to identify and sort a population of NSCs capable of differentiation into mature cell types. After separation, aid purification of such undifferentiated or partially differentiated NSCs, the cells can be cultured in physiological buffer or culture medium and induced to differentiate by culturing in the presence of appropriate factors. For example, basic fibroblast growth factor can be added to induce the NSCs to divide and proliferate and/or differentiate. Such growth factors have the potential to change the pattern of NSC differentiation. Cells can be washed, resuspended in, for example, buffered saline and reintroduced into a patient via, preferably, intravenous administration. The cells can also be used to identify new growth factors (either naturally occurring in a subject or following natural product screening or the screening of a chemical library) which can be used to induce proliferation, differentiation and/or maintenance of endogenous stem cells.

Separation techniques can be utilized which separate and purify NSCs in vitro, from a population of neural cells comprising NSCs. The NSCs may be endogenous to the animal or patient being treated or may be derived from a non-endogenous source. An initial NSC containing population of cells, such as a population of cells derived from neural tissue, can be obtained using standard procedures well shown to those of skill in the art. Particularly useful sources of NSCs include but are not limited to brains or CNS from a range of animals such as primates, humans, livestock animals (e.g. sheep, cows, horses, pigs, etc.) and laboratory test animals (e.g. mice, rats), porcine and bovine brains and can be utilized as potential starting sources for the purification of NSCs. The population may comprise pluripotent NSCs or a mixture of pluripotent or non-pluripotent NSCs or may comprise substantially all committed NSCs.

Once the starting source of nervous tissue is obtained, NSCs can be removed, and thus selectively separated and purified, by various methods which utilize, for example, antibodies and cell surface markers. In these methods, antibodies or molecules that selectively bind to specific marker molecules present on the NSCs population of interest, but do not bind to other cells within the starting source. The bound molecule then acts as a flag to signal the identification of the appropriate NSCs type. These techniques can include, for example, flow cytometry using a fluorescence activated cell sorter (FACS) and specific fluorochromes, biotin-avidin or biotin-streptavidin separations using biotin conjugated to cell surface marker-specific antibodies and avidin or streptavidin bound to a solid support such as affinity column matrix or plastic surfaces or magnetic separations using antibody-coated magnetic beads.

In an alternative method, which is particularly efficient for the practice of the present invention, a negative selection protocol is adopted. In a negative selection, the markers are on cell types other than NSCs. Consequently, non-NSCs are removed.

Therefore, separation via cell surface marker discrimination utlizes antibodies or other molecules which selectively bind specific markers and can be achieved by negative or positive selection procedures. In negative separation, antibodies are used which are specific for markers present on undesired cells. For example, in the case of a pluripotent NSC population wherein it would be desirable to deplete the number of non-pluripotent NSCs. In this case, antibodies could be directed to the extracellular domain of proteins not present on pluripotent NSCs. Cell surface markers suitable for such a method of cell surface discrimination include but are not limited to S100, β-tubulin type III and O4 amongst many others (see below). Alternatively, it may be desirable to directly select pluripotent or non-pluripotent NSCs from a population of nerve cells. In this case, antibodies or other molecules that selectively bind an extracellular domain of a cell surface protein can be used. Cells bound by such an antibody to such a cell surface marker can be sorted and the remaining cells removed and the desired mixture retained.

The cell surface markers used for cell discrimination means may be labeled with a fluorescent compound. When the fluorescently labeled antibody or molecule with selective binding capacity is exposed to light of the proper wavelength, its presence can then be detected due to fluorescence. Among the most commonly used fluorescent labeling compounds are fluorescein isothiocyanate, rhodamine, isothiocyanate, phycoerythrin, phycocyanin, allophycocyanin, o-phthaldehyde and fluorescamine. The antibody or molecule with selective binding capacity can also be detectably labeled using fluorescence emitting metals such as $^{152}$Eu or others of the lanthanide series. These metals can be attached to the antibody or molecule with selective binding capacity using such metal chelating groups as diethylenetriaminepentacaetic acid (DTPA) or ethylenediamineteraacetic acid (EDTA). The antibody also can be detectably labeled by coupling it to a chemiluminescent compound. The presence of the chemiluminescent-tagged antibody or molecule with selective binding capacity is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester. Likewise, a bioluminescent compound can be used to label the antibody or molecule with selective binding capacity of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labelling are luciferin, luciferase and aequorin. All such methods of labelling an antibody or a molecule with selective binding capacity are contemplated by the present invention.

NSCs capable of proliferation and/or differentiation may be selected from a population of size discriminated cells. Size selection may be simultaneous or sequential to the means of cell surface discrimination. Particularly preferred cell surface markers useful for cell surface discrimination include but are not limited to PNA and HSA. It is preferable that size discriminated NSCs which are from about 5 to about 50 microns are simultaneously or sequentially subjected to cell surface marker discrimination means, wherein NSCs which are from about 5 to about 50 microns in diameter are also phenotypically PNA$^{lo}$ HSA$^{lo}$.

In particular, the subject inventors have identified three populations of cells of which one is substantially homogenous for NSCs, another comprises some progenitor cells whereas the third comprises substantially all differentiated cells.

The populations are described phenotypically as follows:-

| | |
|---|---|
| HSA$^{lo}$ PNA$^{lo}$ | substantially homogenous for NSCs |
| HSA$^{hi}$ PNA$^{lo}$ | comprises some progenitor cells |
| HSA$^{lo}$ PNA$^{hi}$ | substantially homogenous |
| HSA$^{hi}$ PNA$^{hi}$ | differentiated cells |

The HSA$^{lo}$ PNA$^{lo}$ populations of cells may be further characterized as having low levels of the markers listed in Table 3. Low level intracellular markers include β-tubulin type III and 04.

TABLE 3

PNA$^{lo}$ HSA$^{lo}$ cell surface markers which are low on NSC population

| CELL SURFACE MARKER | DESCRIPTION |
|---|---|
| CD3e | T-cell receptor |
| CD4 | T-cells and lymphocytes (helper T cells) |
| CD8a | T-cells |
| CD11b | Granulocytes, macrophages, dendritic cells, NK cells (also known as MAC-1) |
| CD19 | B-cells |
| CD24 | RBC, granulo-, mono-, lymphocytes |
| mCD30.1 | Activated T-cells (TNF receptor family) |
| CD31 | Endothelial cells (platelet endothelial CAM-1) |
| CD34 | Glycosylated transmembrane glycoprotein which acts as a putative HSC marker |
| CD41 | Platelet, megakaryocytes |
| CD45R | B lymphocytes (aka B220) |
| CD45RA | B lymphocytes |
| CD45RB | B lymphocytes |
| CD45RC | B lymphocytes |
| CD45RO | B lymphocytes |
| CD89 | Granulocytes, monocytes/macrophages |
| CD90.2 | T cells (aka Thy1.2) |
| CD99R | T-cell adhesion molecule |
| CD117 | Stem cell/steel/mast-cell factor receptor (aka c-Kit) acts as a co-mitogen for HSCs |
| CD135 | Protein tyrosine kinase related to c-Kit (aka Flk-2/Flt-3) |
| H-2K$^b$ | MHC class I antigen (C57B1/6J) |
| Sca-1 | expressed on mouse HSCs (aka Ly-6A/E) |

Accordingly, the present invention contemplates a method for generating a substantially homogeneous population of NSCs which are from about 5 to about 50 microns in diameter and are phenotypically PNA$^{lo}$ HSA$^{lo}$ from a biological sample, said method comprising subjecting said biological sample or a sub-sample thereof to tissue-disruption means to provide a mixed population comprising the NSCs to be purified, subjecting said mixed population of cells to cell size-discrimination means to generate a population of cells wherein substantially all cells are from about 5 to about 50 microns in diameter and simultaneously or sequentially with the size-discrimination step, subjecting said population to NSCs surface marker-discrimination means to generate a substantially homogeneous population of NSCs which are from about 5 to about 50 microns in diameter and are phenotypically PNA$^{lo}$ HSA$^{lo}$.

Other markers such as those listed in Table 3 may also be used to either characterize the NSCs or to purify the NSCs. In addition, cells phenotypically HSA$^{lo}$ PNA$^{lo}$ express DCC, neogenin, Notch 1, 2 and 3. Plx1 and Sox2; these cells have reduced levels of p75 and Trkβ; these cells do not express or express very low levels of EphA4, TrkA, TrkC, LIFRβ, gp130, ζ1, SOCS2, Pax6, Tbr1, Dlx2, SCL, Burp1 and Sca-1

Reference herein to "phenotypically" refers to the physical constitution of an organism or cell that is determined by the interaction of its genetic component with the environment. "Phenotypic" characteristics are detectable and permit the identification and grouping of cells or organisms with like characteristics. In the present invention, the phenotype of the cell surface characteristic of NSCs is used to distinguish NSCs from more differentiated or committed cell types.

Reference herein to PNA$^{lo}$ and/or HSA$^{lo}$ refers to an NSC with a phenotype that comprises a low presence of or an absence of surface PNA and/or a surface HSA.

In another embodiment of the present invention, there is provided a substantially homogeneous population of NSCs which are from about 5 to about 50 microns in diameter and which are phenotypically PNA$^{lo}$ HSA$^{lo}$ prepared by the method of comprising subjecting a biological sample or a sub-sample thereof to tissue-disrupting means to provide a mixed population comprising the NSCs, subjecting said mixed population of cells to cell size-discrimination means to generate a population of cells wherein substantially all cells are from about 5 to about 50 microns in diameter and simultaneously or sequentially with the size-discrimination step, subjecting said population to NSCs surface marker-discrimination means to generate a substantially homogeneous population of NCSs which are from about 5 to about 50 microns in diameter that are phenotypically PNA$^{lo}$ HSA$^{lo}$.

It is preferable that the population of NSCs used to replace or repair neural or non-neural tissue are from about 5 to about 50 microns in diameter and are phenotypically PNA$^{lo}$ HSA$^{lo}$.

The present invention contemplates, therefore, a method for the replacement of neural or non-neural tissue in an animal, said method comprising, generating a substantially homogeneous population of NSCs which are from about 5 to about 50 microns in diameter and are phenotypically PNA$^{lo}$ HSA$^{lo}$ from a biological sample, said method comprising subjecting said biological sample or a sub-sample thereof to tissue-disrupting means to provide a mixed population comprising NSCs, subjecting said mixed population of cells to cell size-discrimination means to generate a population of cells wherein substantially all cells are from about 5 to about 50 microns in diameter and simultaneously or sequentially with the size-discrimination step, subjecting said population to cell surface marker discrimination means to generate a substantially homogeneous population of NSCs which are from about 5 to about 50 microns in diameter that are phenotypically PNA$^{lo}$ HSA$^{lo}$ and then introducing said homogeneous population of NSC which are from about 5 to about 50 microns in diameter and are phenotypically PNA$^{lo}$ HSA$^{lo}$ to said same animal or an animal capable of receiving said NSCs.

Again, an "animal" includes a human or primate, amongst others.

Neurodegenerative diseases and acute brain injuries often result in the loss of neural cells, the inappropriate functioning of the affected brain region, and subsequent behaviour abnormalities. Probably the largest area of CNS dysfunction (with respect to the number of affected people) is not characterized by a loss of neural cells but rather by an abnormal functioning of existing neural cells. This may be due to inappropriate firing of neurons, or the abnormal synthesis, release, and processing of neurotransmitters. These dysfunctions may be the result of well studied and characterized disorders such as depression and epilepsy, or less understood disorders such as neurosis and psychosis. The present invention contemplates a composition comprising NSCs to replace neural tissue. Preferably, the composition of cells of differentiating into neural and regenerating NSCs which are from about 5 to about 50 microns in diameter and are phenotypically PNA$^{lo}$ HSA$^{lo}$.

In this embodiment, the present invention provides a composition for use in neural tissue replacement therapy, said composition comprising a population of substantially homogeneous NSCs which are from about 5 to about 50 microns in diameter and are phenotypically PNA$^{lo}$ HSA$^{lo}$ prepared by the method of generating a substantially homogeneous population of NSCs which are from about 5 to about 50 microns in diameter and are phenotypically PNA$^{lo}$ HSA$^{lo}$ from a biological sample, said method comprising subjecting said biological sample or a sub-sample thereof to tissue-disrupting means to provide a mixed population comprising NSCs, subjecting said mixed population of cells to cell size-discrimination means to generate a population of cells wherein substantially all cells are from about 5 to about 50 microns in diameter and simultaneously or sequentially with the size-discrimination step, subjecting said population to cell surface marker discrimination means to generate a substantially homogeneous population of NSCs which are from about 5 to about 50 microns in diameter and are phenotypically PNA$^{lo}$ HSA$^{lo}$.

Damaged tissue or dysfunctional neural tissues can be replaced or regenerated by the appropriate proliferation and/or differentiation and/or self-renewal of NSCs. Increasing numbers of undifferentiated cells such as NSCs are required to replace or repair increasingly larger areas of damaged neural tissue. In this aspect of the invention genetically modified NSCs may be provided with additional genetic characteristics as drug resistance or characteristics that increase the longevity of cells during purification. Accordingly, the present invention contemplates the generation of a substantially homogeneous population of genetically modified NSCs which are from about 5 to about 50 microns in diameter and are phenotypically PNA$^{lo}$ HSA$^{lo}$.

Accordingly, the present invention contemplates a method for generating a substantially homogeneous population of genetically modified NSCs which are from about 5 to about 50 microns in diameter and are phenotypically PNA$^{lo}$ HSA$^{lo}$ from a biological sample, said method comprising subjecting said biological sample or a sub-sample thereof to tissue-disruption means to provide a mixed population comprising the genetically modified NSCs to be purified, subjecting said mixed population of cells to cell size-discrimination means to generate a population of cells wherein substantially all cells are from about 5 to about 50 microns in diameter and simultaneously or sequentially with the size-discrimination step, subjecting said population to NSCs surface marker-discrimination means to generate a substantially homogeneous population of NSCs which are from about 5 to about 50 microns in diameter and are phenotypically PNA$^{lo}$ HSA$^{lo}$.

As used herein, the term "genetically modified NSCs" refers to NSCs into which a foreign (i.e., non-naturally occurring) nucleic acid, e.g., DNA, has been introduced. The foreign nucleic acid may be introduced by a variety of techniques, including, but not limited to, calcium-phosphate-mediated transfection, DEAE-mediated transfection, microinjection, retroviral transformation, protoplast fusion and lipofection. The genetically modified cell may express the foreign nucleic acid in either a transient or long-term manner. In general, transient expression occurs when foreign DNA does not stably integrate into the chromosomal DNA of the transfected cell. In contrast, long-term expression of foreign DNA occurs when the foreign DNA has been stably integrated into the chromosomal DNA of the transfected cell.

In a preferred aspect, the NSCs are phenotypically PNA$^{lo}$ HSA$^{lo}$.

In another embodiment of the present invention, there is provided a substantially homogeneous population of genetically modified NSCs which are from about 5 to about 50 microns in diameter and are phenotypically PNA$^{lo}$ HSA$^{lo}$ prepared by the method of comprising subjecting a biological sample or a sub-sample thereof to tissue-disrupting means to provide a mixed population comprising the genetically modified NSCs, subjecting said mixed population of cells to cell size-discrimination means to generate a population of cells wherein substantially all cells are from about 5 to about 50 microns in diameter and simultaneously or sequentially with the size-discrimination step, subjecting said population to NSCs surface marker-discrimination means to generate a substantially homogeneous population of genetically modified NSCs which are from about 5 to about 50 microns in diameter that are phenotypically $PNA^{lo}\ HSA^{lo}$.

In a related embodiment, the present invention provides a method for the replacement of neural tissue in an animal, said method comprising, generating a substantially homogeneous population of genetically modified NSCs which are from about 5 to about 50 microns in diameter and are phenotypically $PNA^{lo}\ HSA^{lo}$ from a biological sample, said method comprising subjecting said biological sample or a sub-sample thereof to tissue-disrupting means to provide a mixed population comprising genetically modified NSCs. subjecting said mixed population of cells to cell size-discrimination means to generate a population of cells wherein substantially all cells are from about 5 to about 50 microns in diameter and simultaneously or sequentially with the size-discrimination step, subjecting said population to cell surface marker discrimination means to generate a substantially homogeneous population of genetically modified NSCs which are from about 5 to about 50 microns in diameter that are phenotypically $PNA^{lo}\ HSA^{lo}$ and then introducing said homogeneous population of genetically modified NSCs which are from about 5 to about 50 microns in diameter and are phenotypically $PNA^{lo}\ HSA^{lo}$ to said same animal or an animal capable of receiving said NSCs.

As stated above, the preferred size is from about 7 to about 30 microns although a size of greater than 12 microns is particularly useful.

The substantially homogeneous population of NSCs described herein can be administered to a patient at a therapeutically effective dose to treat or ameliorate disorders of the nervous system including for repair or replacement of nervous tissue. A therapeutically effective dose refers to that amount of a substantially homogeneous population of NSCs sufficient to result in amelioration symptoms of a nervous system disorder.

Toxicity and therapeutic efficacy of a substantially homogeneous population of NSCs can be determined by standard and modified pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. A substantially homogeneous population of NSCs which exhibits large therapeutic indices are preferred. It is formally possible that NSCs may exhibit toxic side effects by eliciting an immune response, care should be taken to design a delivery system that prevents detrimental immune responses.

The data obtained from the cell culture assays and animal studies can be used in formulating a range of dosage for use in humans. The dosage of such substantially homogeneous population of pluripotent NCSs lies preferably within a range of concentrations that include the $ED_{50}$ with little or no toxicity. The dosage can vary within this range depending upon the dosage form employed and the route of administration utilized. For any substantially homogeneous population of NSCs used in the method of the invention, the therapeutically effective dose can be estimated initially from cell culture assays.

Pharmaceutical compositions for use in accordance with the present invention can be formulated in conventional manner using one or more physiologically acceptable carriers or excipients. Thus, the substantially homogeneous population of NCSs and their physiologically acceptable salts and solvents can be formulated for administration by a range of routes including injection or oral delivery.

As described herein, the NCS populations generated by the subject methods have a range of utilities. Other utilities contemplated by the present invention include putting a marker on or within a NSC and then using this to track the NSC and/or its progeny throughout the body and to monitor is physiological changes. This provides an ability to direct therapies to multiple targets. The purified populations of NSCs are also useful for gene and protein discovery and in particular the mechanisms involved in differentiation and proliferation. This enables the therapeutic production of new neurons in various disease states.

Furthermore, the NSCs of the present invention are useful in cytokine delivery via, for example, endogenous stem cell activation and for selective migration of NSCs and their progress to sites of injury.

All such uses of the subject NSCs are contemplated by the present invention.

The purified stem cells may also be used to screen for molecules which can influence the growth, proliferation and/ or differentiation of stem cells. The significance of such factors is that:

1. with "unpure" populations, it cannot be determined that the effect is directly on the stem cell and not via other molecules; and
2. thus information allows therapeutics to be developed which can be used to activate the endogenous stem cell to differentiate into new neurons or glia and the like.

Thus, this aspect of the present invention does not require transplantation to occur. Such molecules would, however, be an important adjunct to successful transplantation therapy.

Accordingly, the present invention is further directed to isolating growth factors capable of facilitating NSC growth, proliferation and/or differentiation, said growth factors obtainable from the homogeneous population of NSCs prepared according to the method herein described.

Furthermore, the present invention identifies a population of NSCs which become neuronal cells. Accordingly, the present invention encompasses a naturally occurring agonist (e.g. a cytokine) or a molecule found through natural product screening or through screening of a chemical library which act on the subject population of cells. Such agents and methods of use are encompassed by the present invention.

The present invention is further described by the following non-limited examples:

EXAMPLE 1

Tissue Preparation

Adult mice (8-10 weeks old) were sacrificed by cervical dislocation CNS tissue dissected into Hepes buffered Eagle's medium (HEM) essentially as per Lois and Alvarez-Buylla, (*Proc. Natl. Acad. Sci. USA* 90, 2074-2077, 1993). Both the ventricular and sub-ventricular (SVZ) zones of the lateral ventricular walls of adult CBA mice were used as the source of NSC. CNS tissue was diced then transferred to $Mg^{++}/Ca^{++}$ free HBSS (containing 10 mM Hepes, 200 g/ml EDTA, 0.5 mM trypsin, 0.001% w/v DNase; pH 7.6, for 10 minutes at 37° C. 6 mls of HEM+5% v/v fetal calf serum (FCS) was added and the tissue pieces collected by centrifugation (7 minutes at 100×g), Supernatent was removed and pellet triturated in PBS (pH 7.4) to produce a single cell suspension which was subsequently passed through a 70 μM cellstrainer (Falcon) to remove debris.

Following enzymatic dissociation, single cell suspensions were stained with a variety of antibodies and lectins then sorted using a FACS II (Becton-Dickinson, USA) flow cytometer.

EXAMPLE 2

FACS Analysis

For immunostaining, the resulting suspension was incubated for 20 minutes at 4° C. with FITC conjugated PNA (1:200; Vecta, Burlingame, Calif.), or PNA-FITC combined with PE-conjugated mCD24a (1:200; Clone M1/69, Pharmingen). Following incubation, the cell suspension was rinsed twice with PBS via centrifugation, and finally in PBS÷1% v/v FCS Propidium Iodide (P.I.; 100 pg/ml; Molecular Probes) to label dead cells before FACS analysis. Cell viability was typically greater than 95% and all FACS gates were set using unlabelled cells.

An initial NSC enrichment step was accomplished by sorting viable cells on the basis of their size as assessed by forward light scatter (FSC) [FIG. 1A] It was found that >80% of the total NSCs present in the unsorted population were contained in the cells of >12 μm in diameter (>90 units FSC). Next, the differential binding of a lectin, peanut agglutinin (PNA), was used to selectively enriched for NSCs. From the FACS profiles comparing cell diameter (FSC) and PNA staining intensity, 3 populations were chosen for assessing NSC content: $PNA^{hi}$, $PNA^{lo}$ and $PNA^{mid}$ fractions [FIG. 1A]. The >12 μm $PNA^{lo}$ fraction, which represents approximately 2% of the unsorted population, contained the greatest NSC activity with approximately 1:7 cells a NSC.

The final enrichment step was using Heat Stable Antigen [HSA] (mCD24a) to effectively enrich for NSCs in subpopulations of $PNA^{lo}$ cells. The $PNA^{lo}$ $HSA^{lo}$ sub-population [FIGS. 1B and 1C], a discrete population representing 0.27±0.07% (mean SE; n=3) of the unsorted population, was found to be comprised almost exclusively of NSC.

EXAMPLE 3

FACS Analysis and Characterization of $PNA^{lo}$ $HSA^{lo}$ NSCs

To examine the phenotype of the $PNA^{lo}$ $HSA^{lo}$ NSCs more closely, sorted cells were immunostained for other neural markers. $PNA^{lo}$ $HSA^{lo}$ NSCs expressed nestin, a marker of putative neural stem and precursor cells (Calaora et al, *Neuroscience* 73: 581-594 1996), however, they did not express the cell type specific neural markers (β-tubulin type III, 04 or GFAP).

EXAMPLE 4

Morphological Analysis

The $PNA^{lo}$ $HSA^{lo}$ NSCs did not have the ciliated morphology of ependymal cells, previously implicated as the origin of NSCs. Further since ependymal cells have been previously shown to express high levels of HSA, this favors the conclusion of others that the vast majority of stem cells reside in the SVZ (Tropepe el al., *J. Neurosci.* 17: 7850-7859, 1997).

EXAMPLE 6

Generation of Neurospheres

To assess the stem-like nature of sorted cells harvested from CNS tissue, neurospheres were generated as previously described (Gritti et al., *J. Neurosci.* 19: 3287-3297, 1999). Essentially, sorted cells were plated in growth factor free defined NS-A media (basal media; consisting of Dulbecco's Modified Eagles Medium (DMEM) with a nutrient supplement F12 (Gibco) (1;1) and containing 0.6% glucose, 3 mM $NaHCO_3$, 5 mM HEPES, and 2 ml L-glutamine, 0.1 mg/ml apo-transferrin, 25 μg/ml insulin, 60 μM putrescene, 30 mM sodium selenite and 20 nM progesterone (Sigma))(1,10) containing FGF-2 (bovine 20 recombinant, 10 ng/ml; Boehringer Mannheim) and EGF (receptor grade, 20 ng/ml; Collaborative Research) either at a density of 10 viable cells/cm² to ascertain NSC frequency and enrichment, or at 1 cell per well to determine the precise NSC frequency. Counting the number of spheres formed after seven days in vitro (DIV) as compared to number of cells plated yielded the NSC frequency.

Where one $PNA^{lo}$ $HSA^{lo}$ cell was plated per well, approximately 80% of the cells (1:1.28) gave rise to neurospheres. Furthermore, the $PNA^{lo}$ $HSA^{lo}$ population contained >63% of the NSC activity present in the unsorted population {% recovery=% of total cells×(NSC frequency unsorted=NSC frequency sorted)} strongly suggesting that the vast majority of the NSCs in the ventricular zone of adult mice are of this phenotype.

Subsequent passaging of primary spheres was performed by mechanically dissociating harvested spheres (centrifuged 10 min. at 100×g) into a single-cell suspension and replating in basal media containing EGF+FGF-2 (complete media) as described by Reynolds et al., 1992 (supra; Gritti et al., *J. Neurosci.* 16. 1091-1100, 1996).

EXAMPLE 7

Neural Cell Potential of $PNA^{lo}$ $HSA^{lo}$ Cells

Figure 3A:
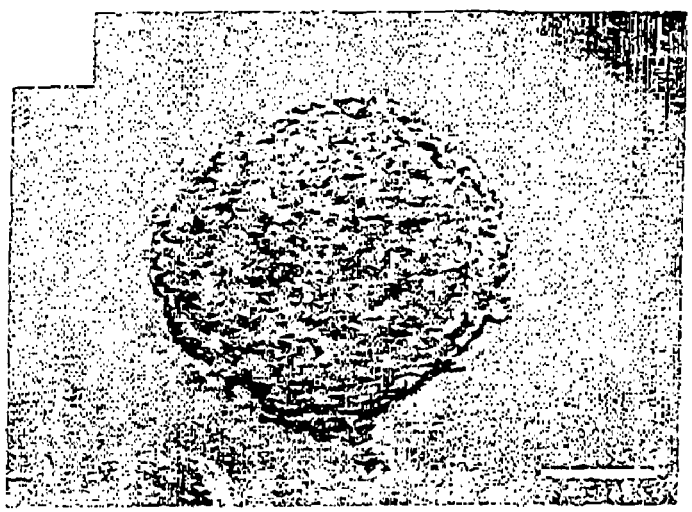
FIG. 3 is a photographic representation of PNA$^{lo}$ HSA$^{lo}$ adult NSCs give rise to undifferentiated (neurospheres) and differentiated neural and muscle cell types. A single PNA$^{lo}$ HSA$^{lo}$ cell proliferates to form, neurospheres [3A] whose progeny, when transferred to differentiating conditions [3B], includes neurons (red, β-III-tubulin) and astrocytes (blue, GFAP) and oligodendrocytes (green, 04). When co-cultured with C2C12 cells, freshly isolated GFP$^{+ve}$ PNA$^{lo}$ HSA$^{lo}$ NCSs assume a spindle-like morphology [3C-D] and often possess multiple DAPI$^{+ve}$ nuclei (arrow, [3D]) suggestive of muscle cells. Myogenic conversion of NSCs was confirmed by anti-MyHC developmental- (red, [3E]), anti-α-actinin 2- (red, [3F]) and anti-Type 2 NyHCfast- (red, [3G, H]) immunoreactive cells containing GFP$^{+ve}$ nuclei and cytoplasm. In most cases, immunostaining procedures reduced the intensity of cytoplasmic GFP to below detectable levels, thus GFP expression was found predominantly in the nucleus. Bars: (a)=80, (b,c,g)=40, (d)=20, (e,h)=10 and (f)=15 μm. Color versions of this photograph are available from the patentee.
Figure 3B:

Clonally-derived spheres from $PNA^{lo}$ $HSA^{lo}$ cells [FIG. 3A] were differentiated by transfer to poly-L-omithine coated glass coverslips (1 sphere per coverslip) in basal media for 1 day then basal media+1% v/v FCS for 5-6 days, then assessed by immunocytochemistry (ICC) for the presence of neurons and glia. In 100% of cases, clonally derived spheres contained glial fibrillary acidic protein positive ($GFAP^{+ve}$) astrocytes and (β-tubulin type III positive ($β-tub^{+ve}$) neurons and $04^{+ve}$ oligonucleotides [FIG. 3B].

To determine whether clonally-derived spheres from $PNA^{lo}$ $HSA^{lo}$ cells retained this potential after continued proliferation, secondary spheres were passaged every 5-7 DIV for 3 months, then transferred to differentiating conditions. Once again, $GFAP^{+ve}$ and $3-tubulin^{+ve}$ cells and $04^{+ve}$ cells were present in every sphere examined.

EXAMPLE 8

Characterization of Cells

To determine whether freshly isolated $PNA^{lo}$ $HSA^{lo}$ NSCs had the potential to give rise to non-neural cell types, a recently developed assay system was used which which enables a quantitative assessment of the myogenic potential of individual NSCs (Galli et al., *Nature Neuroscience* 3: 2000). To easily identify the NSCs amongst the C2C12 cells, $PNA^{lo}$ $HSA^{lo}$ NSCs were isolated from BU5X transgenic mice which ubiquitously express both lacZ (22) and enhanced GFP (Hadjantonakis et al., *Mech. Dev.* 76: 79-90, 1998). The $PNA^{lo}$ $HSA^{lo}$ NSCs from the BU5X mice showed identical characteristics to that from the CBA.

Freshly isolated NSCs were assessed for their myogenic potential by co-culturing them at a clonal density in vitro with the C2C12 myogenic cells (5×10³ cells/cm²) for two days in DME media (Gibco) containing 20% v/v heat inactivated FCS, then in DME supplemented with 10%, v/v normal horse serum (CSL, Australia) for an additional 2-4 DIV. Cultures were then fixed for 5 minutes with 4% v/v paraformaldehyde and then the phenotype of the GFP$^{+ve}$ cells was assessed.

Neural derived muscle cells were identified by simultaneous detection of endogenous GFP and muscle cell types identified by mouse monoclonal antibodies to MyHCfast or MyHCdevelopmental (NCL-MHCf or NCL-MHCd respectively, both 1:10, Novocastra Labs Ltd.), or α-actinin-225 (1:750, E. Hardeman). These antigens were detected by appropriate TRITC-conjugated IgG secondary antibody (1:200; Southern Biotech). The proportion of neural cells which differentiated into muscle cells was determined by counting the number of GFP$^{+ve}$ nuclei expressing myogenic markers divided by the number of NSCs plated (counted 6 hrs post-plating).

Figure 3C:
Figure 3D:
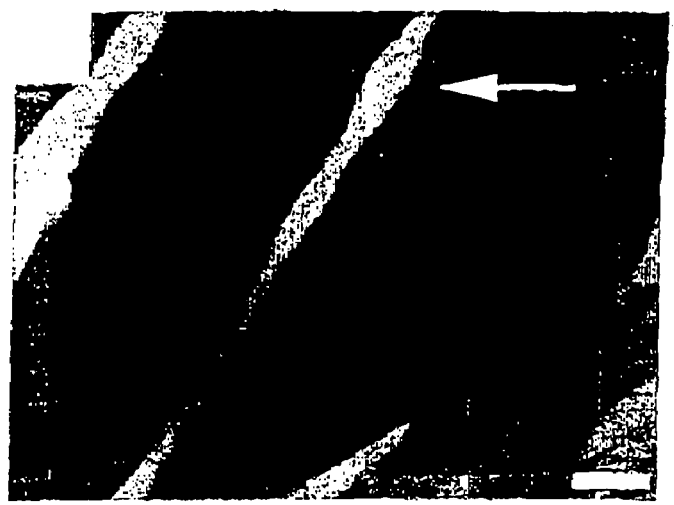
Figure 3E:
Figure 3F:
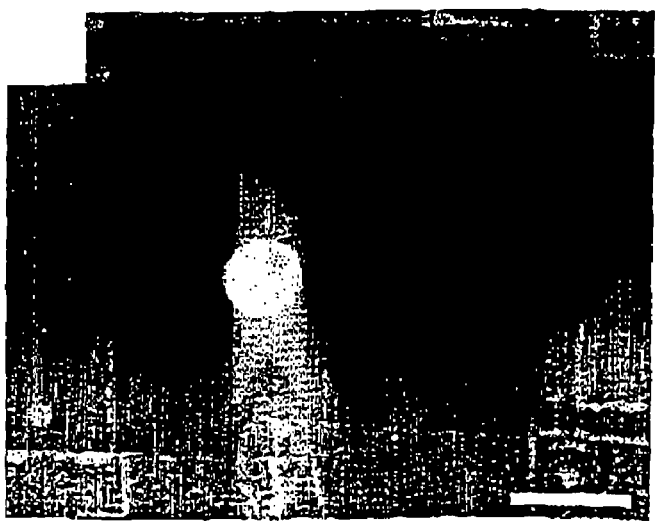
Figure 3G:
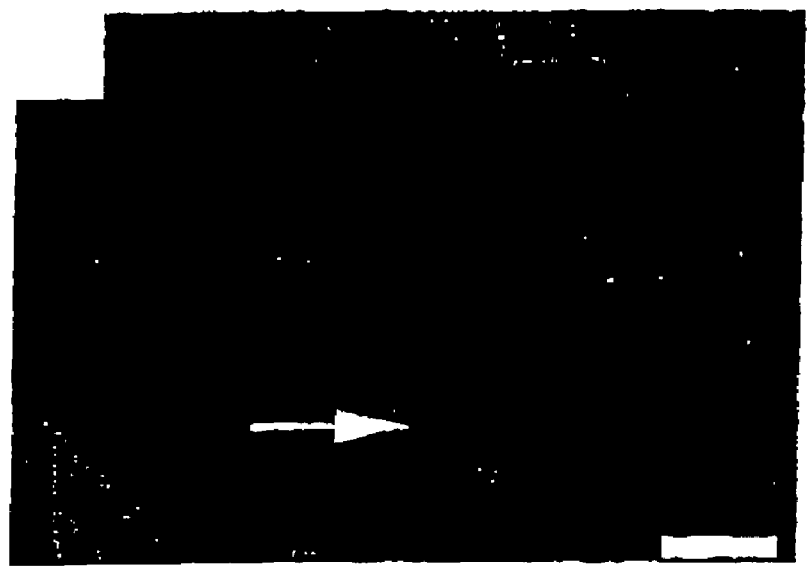
Figure 3H:
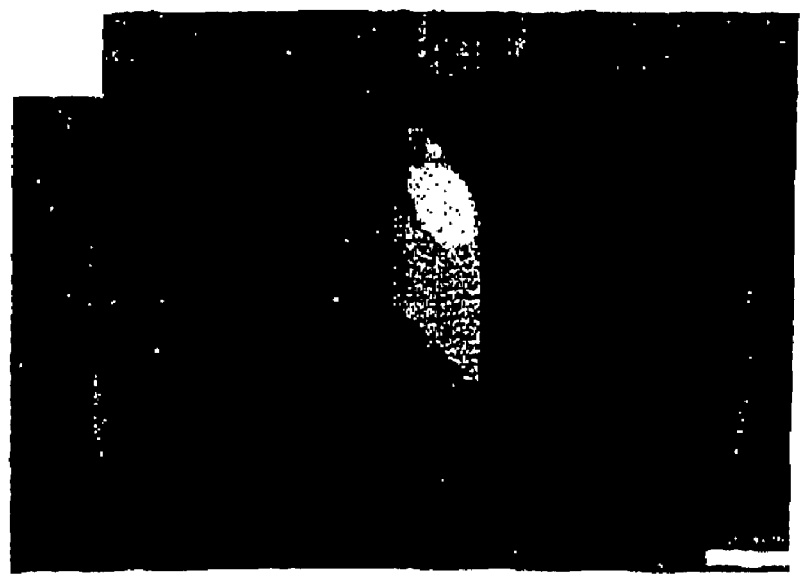
Figure 4:
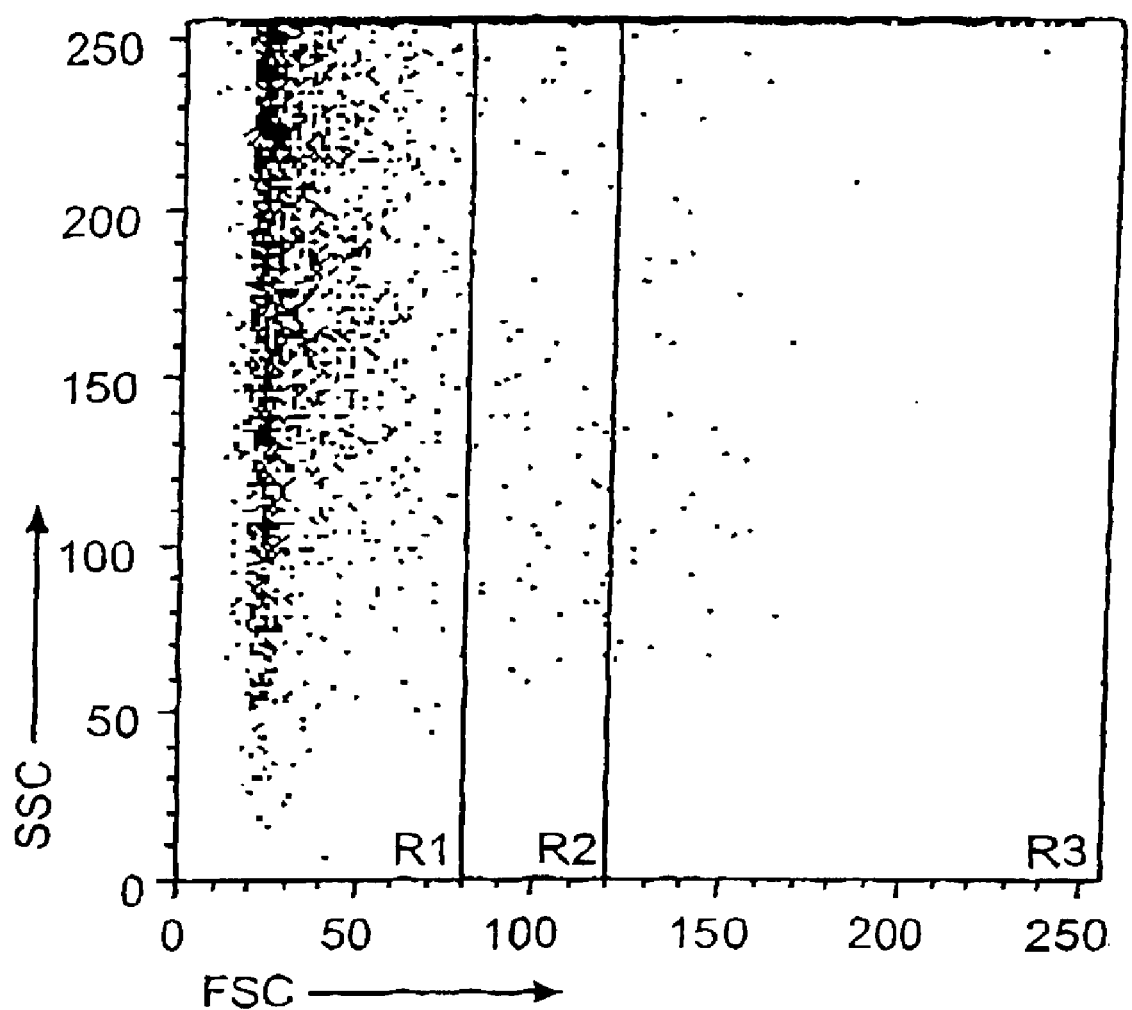
FIG. 4 is a graphical representation of a dot plot showing the FACS sorting of CNS cells harvested from adult human periventricular region. Cells are sorted on the basis of forward light scatter (0-80, 80-120, >120 units) Stem cell activity is confined to R3 (region 3). Percentage of total cells listed below.
Figure 5A:
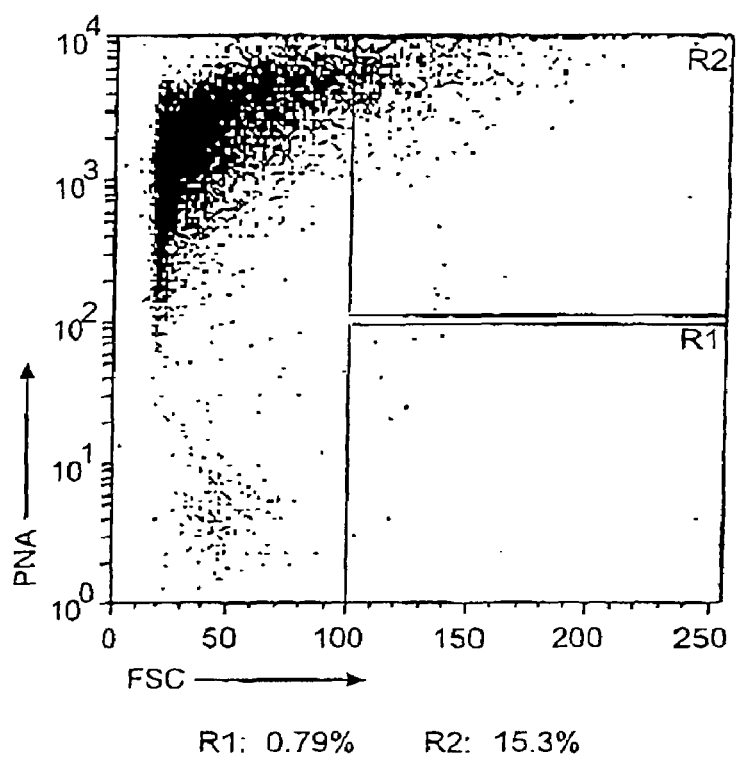
FIG. 5 is a graphical representation of a dot plot showing the FACS sorting of viable CNS cells harvested from adult human periventricular region. (A) Cells are sorted on the basis of forward light scatter (>100 units) and PNA binding ability. Unlike mouse stem cells, adult human stem cell activity is confuted to R2 (region 2). When sorting viable cells which are also >100 units FSC on the basis of PNA binding and HSA expression. (B) The inventors can enrich for stem cell activity by harvesting cells from R5. Cells in R3 have no stem cell activity, while those in R4 most comprise differentiated neural cell types. Percentage of total cells listed below.
Figure 5B:
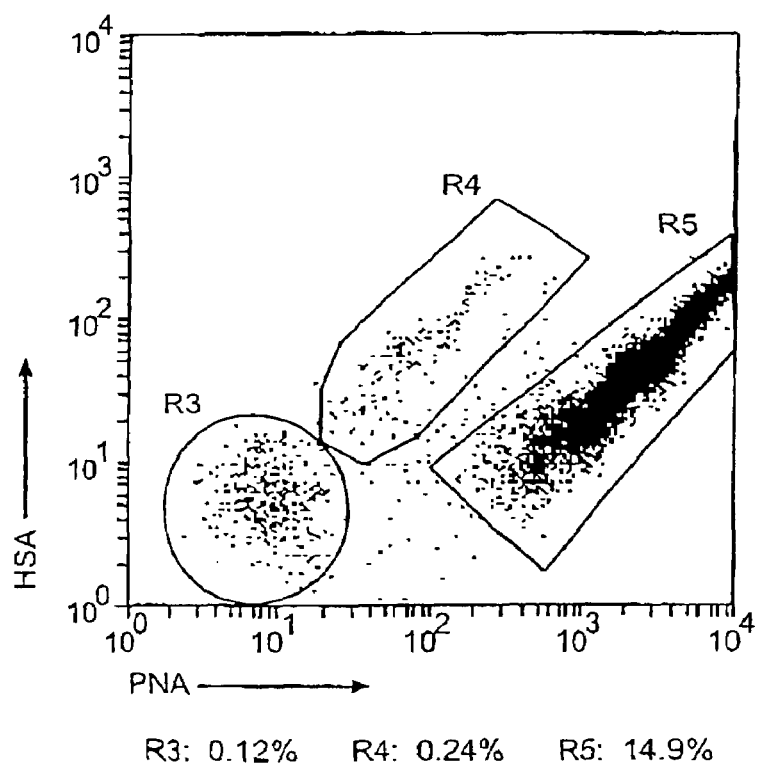

GFP expressing cells assumed a spindle, myocyte-like shape [FIGS. 3C-D and often contained multiple nuclei characteristic of myotubes [arrow, FIG. 3D]. Their muscle phenotype was confirmed by the staining of <99% of the spindle shaped cells and myotubes with myogenic-specific antibodies to α-actinin-2 [FIG. 3F)] and two isoforms of MyHC [FIGS. 3E, G and H]. Most importantly, GFP was found to be co-expressed in cells labelled with myogenic markers [FIG. 3E-H)]. In the case of myotubes, often only 1 bright GFP$^{+ve}$ nucleus was amongst several non-GFP$^{+ve}$ nuclei [FIG. 3(h)] demonstrating unequivocally that some of the PNA$^{lo}$ HSA$^{lo}$ NSCs had differentiated into myocytes or fused with C2C12 cells to form myotubes.

Since there was no evidence of significant cell division occurring after plating of the sorted PNA$^{lo}$ HSA$^{lo}$ NSCs (as-certained by constant monitoring by fluorescent microscopy of GFP$^{+ive}$ cells) the frequency of NSCs with myogenic potential could be directly determined. It was found that 57±5.67% (mean±SE; n=3) of the plated PNA$^{lo}$ HSA$^{lo}$ GFP$^{+ve}$ NSCs differentiated into spindle shaped, MHC$^{+ve}$ myocytes or myotubes (as determined by counting GFP$^{+ve}$ nuclei in myotubes).

EXAMPLE 9

Functional Stem Cells

Figure 2B:
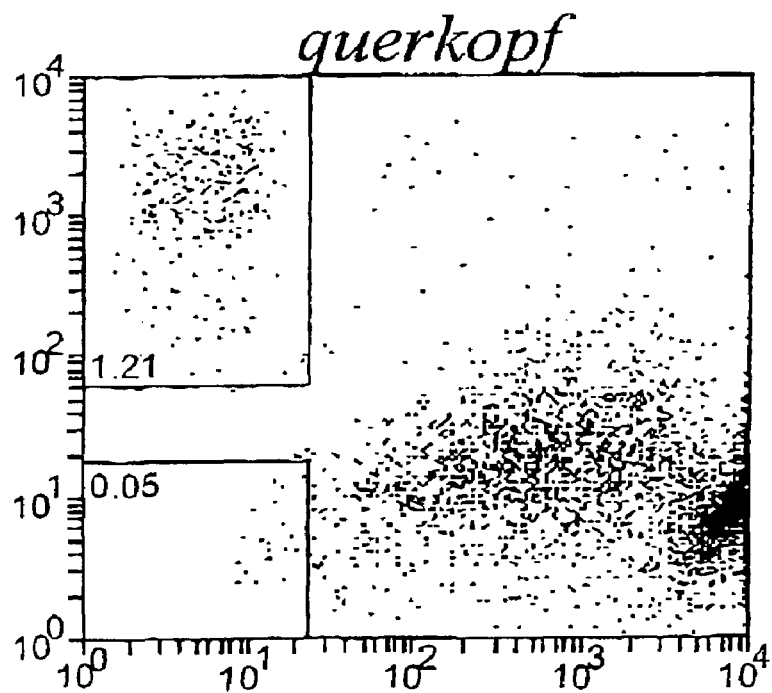
FIG. 2B is a graphical representation of a dot plot showing FACS sorting of viable cells (which are >12 μm or 90 units) by PNA expression and HSA expression. These cells have been harvested from an individual querkopf mutant mouse. Values within gated regions indicates the percentage of cells contained within that region, as compared to overall viable cell number. For example, PNA$^{lo}$ HSA$^{lo}$ cells represent 0.05% while PNA$^{lo}$ HSA$^{mid-hi}$ cells represent 1.21% of overall viable cells.

The following example shows that the cells isolated act as functional NSCs in vivo. The results are shown in Table 4. These data are derived employing the mutant mouse querkopf, which has a mutation in a histone acetyltransferase gene (Thomas et al., *Development* 127: 2537, 2000). The observation of interest for this study is Querkopf's progressive deficiency in the size of the olfactory bulb, when compared to wild-type from the postnatal period onward. Recall that the olfactory bulb grows throughout postnatal life due to the continual migration of cells derived from subventricular region stem cells, which ultimately differentiate into olfactory granule and periglomerular neurons. Thus, the inventors have examined whether the deficiency in querkopf is reflected in the loss of stem cells in the periventricular region, and if so, in which sort population they reside. The inventors found by FACS analysis that the mutant and wild-type profiles are exactly the same except for an approximately 6-fold diminution in the PNA$^{lo}$ HSA$^{lo}$ population (FIG. 2). The frequency of stem cell activity in both wild-type and mutant PNA$^{lo}$ HSA$^{lo}$ populations is not significantly different, indicating that there is no intrinsic difference in the functional capacity of the PNA$^{lo}$ HSA$^{lo}$ stem cell, but that there is a dramatic decrease in their overall number. Furthermore, since no change in stern cell activity can be found in other sorted populations, this could not be explained by a shift in stem cell phenotype. Thus, these data strongly suggest that the deficiency in generating olfactory bulb neurons postnatally in querkopf mice is due to a specific depletion in the PNA$^{lo}$ HSA$^{lo}$ population, further supporting a functional role for these cells in situ.

TABLE 4

Shows flow cytometric analysis fresh NSCs on the basis of size and surface markers.

| Cell phenotype | NSC frequency* |
|---|---|
| Unsorted | 1:300 |
| <7 μm | 0 |
| 7-12 μm | 1:538 |
| >12 μm | 1:149 |
| >12 μm PNA$^{hi}$ | 1:1667 |
| >12 μm PNA$^{mid}$ | 1:87.9 |
| >12 μm PNA$^{lo}$ | 1:6.77 |
| >12 μm PNA$^{lo}$ HSA$^{mid-lo}$ | 1:15.4 ± 2.83 |
| >12 μm PNA$^{lo}$ HSA$^{lo}$ | 1:1.28 ± 0.11 |

These cells were collected and transferred into culture conditions known to generate neurospheres. NSC frequency* represents the number of neurospheres generated after seven divisions per viable cell plated, where viable cells were counted four hrs after plating.

EXAMPLE 10

Markers Defining Cell Populations

A range of primers defining a variety of markers (external and internal) are used to assess and phenotypically characterize populations of cells. The markers and the nucleotide sequence of primers used are shown in Table 5.

Three populations of cells are identified based on expression of HSA and PNA. Each population is then assessed for the markers listed in Table 5. The results are shown in Table 6.

Cells phenotypically HSA$^{lo}$ PNA$^{lo}$ exhibit markers which are characteristic of being a homogenous population of NSCs (Table 6). Cells phenotypically HSA$^{hi}$ PNA$^{lo}$ comprise some progenitors whereas HSA$^{lo}$ PNA$^{hi}$/HSA$^{hi}$ PNA$^{hi}$ cells are substantially all differentiated cells (Table 6).

TABLE 5

Primers used to identify molecules

| Target DNA | Primer Sequence (5'→3') | | Approx. Product Size (bp) | +ve Control Reference No. |
|---|---|---|---|---|
| mβ-actin | S-CTG AAG TAC CCC ATT GAA CAT GGC | [SEQ ID NO:1] | 740 | |
| | AS-CAG AGC AGT AAT CTC CTT CTG CAT | [SEQ ID NO:2] | | |
| hβ-actin | S-ACC GCG AGA AGA TGA CCC AGA T | [SEQ ID NO:3] | | |
| | AS-CAC CTT CAC CGT TCC AGT TTT T | [SEQ ID NO:4] | | |

TABLE 5-continued

Primers used to identify molecules

| Target DNA | Primer Sequence (5'→3') | | Approx. Product Size (bp) | +ve Control | Reference No. |
|---|---|---|---|---|---|
| mEphA4 | S-GCC AAA GAA ATC GAT GCA TCC TGC | [SEQ ID NO:5] | | | 235 |
| | AS-GAC GCT GCT CAA AAT CTT ATT CTG | [SEQ ID NO:6] | | | |
| mDCC | S-CCC AGT CCA AGG TTA CAG ATT | [SEQ ID NO:7] | 570 | E14.5 whole embryo | 720 |
| | AS-GAG GTG TCC AAC TCA TGA TG | [SEQ ID NO:8] | | | |
| MRyk | S-GCC ACA AAG TTG TTC ACT TGG | [SEQ ID NO:9] | 500 | | — |
| | AS-GCT GAC ACA CCC AAC AAT GC | [SEQ ID NO:10] | | | |
| mNeogenin splice#1 | S-GGG GGA TGT GGT TAT CCC CA | [SEQ ID NO:11] | 330 & 390 | E14.5 whole embryo | |
| | AS-GAT GCA GGT GTA CGC CAT GTC | [SEQ ID NO:12] | | | |
| mNeogenin splice#2 | S-GGC GAA GGC ATC CCC CTT TAT | [SEQ ID NO:13] | 140 & 190 | E14.5 whole embryo | |
| | AS-GGG AGT TGT CTG CCC AGG TAA | [SEQ ID NO:14] | | | |
| mNeogenin splice#4 | S-AGG GCA TGA GTC AGA GGA CAG | [SEQ ID NO:15] | 225 & 380 | E14.5 whole embryo | |
| | AS-AGT CTT CCT CTT GGG AGC TGG | [SEQ ID NO:16] | | | |
| mTrkA | S-TGC GCT GGT TGT TCA ACG GC | [SEQ ID NO:17] | | | — |
| | AS-CCC ACT GAA GAA TGA TGT CC | [SEQ ID NO:18] | | | |
| mTrkB | S-ACA CAC AGG GCT CCT TAA GG | [SEQ ID NO:19] | | | — |
| | AS-CAT AGA CCG AGA GAT GCT CC | [SEQ ID NO:20] | | | |
| mTrkC | S-TGC CAT CAA CTT GAC CCT CG | [SEQ ID NO:21] | | | — |
| | AS-AGC AAG TCC GAC TGC TAT GG | [SEQ ID NO:22] | | | |
| mp75 | S-GTG CAC CGA GTG CCT GGG CC | [SEQ ID NO:23] | 530 | p75 Exp. Plmd. cDNA | — |
| | AS-CAC AGC AGC CAA GAT GGA GC | [SEQ ID NO:24] | | | |
| mLIFRβ | S-GCT GTC ATT GTT GGC GTG G | [SEQ ID NO:25] | 160 | E11.5 whole embryo | 934 & 935 |
| | AS-TTC ATT TCC AAT GTT TTA AGA GC | [SEQ ID NO:26] | | | |
| mgp130 | S-GCC CTT GGG AAT GTC TCC TCA GAG | [SEQ ID NO:27] | 450 | E11.5 whole embryo | 933 & 935 |
| | AS-TCT TCC ATA TGA GCC GTG CAG ACC | [SEQ ID NO:28] | | | |
| mNR6 | S-GGA TCG GGA GCC CAC ACA GC | [SEQ ID NO:29] | 360 | | |
| | AS-AGC GGC ACG TGA GAT CCT TC | [SEQ ID NO:30] | | | |
| mNotch1 | S-TTA CAG CCA CCA TCA CAG CCA CAC C | [SEQ ID NO:31] | 380 | E11.5 whole embryo | 928 |
| | AS-ATG CCC TCG ACA CAA TCA GA | [SEQ ID NO:32] | | | |
| mNotch2 | S-GAG GCG ACT CTT CTG CTG TTG AAG A | [SEQ ID NO:33] | 475 | E11.5 whole embryo | 928 |
| | AS-ATA GAG TCA CTG AGC TCT CGG ACA G | [SEQ ID NO:34] | | | |
| mNotch3 | S-ACA CTG GGA GTT CTC TGT | [SEQ ID NO:35] | 470 | E11.5 whole embryo | 928 |
| | AS-GTC TGC TGG CAT GGG ATA | [SEQ ID NO:36] | | | |
| mζ1 | S-TGT GAC GAG GAC TAC TAC GGA GAA G | [SEQ ID NO:37] | 330 | E11.5 whole embryo | 928 |
| | AS-AGT AGT TCA GGT CTT GGT TGC AGA A | [SEQ ID NO:38] | | | |
| mSOCS1 | S-CTC GAG TAG GAT GGT AGC ACG CAA | [SEQ ID NO:39] | 350 | E9.5 whole embryo | 931 |
| | AS-CAT CTT CAC GCT GAG CGC GAA GAA | [SEQ ID NO:40] | | | |
| mSOCS2 | S-GGA ATG GAG CGG ACA GGA CG | [SEQ ID NO:41] | 270 | E14.5 whole embryo | — |
| | AS-GTA CTC AAT CCG CAG GTT AGT C | [SEQ ID NO:42] | | | |
| mSOCS3 | S-ACC AGC GCC ACT TCT TCA CG | [SEQ ID NO:43] | 450 | E14.5 whole embryo | — |
| | AS-GTG GAG CAT CAT ACT GAT CC | [SEQ ID NO:44] | | | |
| mPax6 | S-AAG TCC AGG TGC TGG ACA ATG | [SEQ ID NO:45] | 790 | E11.5 whole embryo | |
| | AS-GCT GTG GGA TTC GCT GGT AG | [SEQ ID NO:46] | | | |
| hPax6 | S-CTC CAC CCG GCA GAA GAT TGT AGA | [SEQ ID NO:47] | | | |
| | AS-CCG GTG TGG TGG GTT GTG GA | [SEQ ID NO:48] | | | |
| mTbr1 | S-CTG ACT CCA AGG ACT CAC CAG | [SEQ ID NO:49] | 690 | E11.5 whole embryo | |
| | AS-TCC AGT GAG CCC CAG TGT TG | [SEQ ID NO:50] | | | |
| hTbr1 | S-CCC GCC TGC ATG TGG TGG AAG T | [SEQ ID NO:51] | | | |
| | AS-GGG CGG CCT AGC TGT GCG AGT A | [SEQ ID NO:52] | | | |

TABLE 5-continued

Primers used to identify molecules

| Target DNA | Primer Sequence (5'→3') | | Approx. Product Size (bp) | +ve Control | Reference No. |
|---|---|---|---|---|---|
| mSvet1 | S-CCC TCT GGC GGT ATA GGG AA | [SEQ ID NO:53] | 860 | | |
| | AS-GGC CTC TTC CTC TCA TAC CTG | [SEQ ID NO:54] | | | |
| mNkx2.1 | S-GAC GTG AGC AAG AAC ATG GC | [SEQ ID NO:55] | | | |
| | AS-GCT GGA GAC CTG GCC CTG C | [SEQ ID NO:56] | | | |
| mDlx1 | S-AAG AAC ACC TGG CCA AGA AGA AAA AT | [SEQ ID NO:57] | 450 | E9.5 whole embryo | |
| | AS-CCC CCA AGA TAC AAA GCA ATA AG | [SEQ ID NO:58] | | | |
| mDlx2 | S-AAC ACT CCC GTA GCT CCT TCA TCC A | [SEQ ID NO:59] | 320 | E9.5 whole embryo | |
| | AS-CTA CGT CGC AGC TTT CAC AAC TCG | [SEQ ID NO:60] | | | |
| mSox1 | S-GCC GCG CCG CAA GAC CAA GAC | [SEQ ID NO:61] | 480 | | |
| | AS-CGC CGT AAG GGA TGC CGC CGT AGC | [SEQ ID NO:62] | | | |
| mSox2 | S-CGG GGG CAG CGG CGT AAG AT | [SEQ ID NO:63] | 540 | E9.5 whole embryo | |
| | AS-GGG TGC CCT GCT GCG AGT AG | [SEQ ID NO:64] | | | |
| mEmx1 | S-AAT CAC TAC GTG GTG GGA GC | [SEQ ID NO:65] | 130 | | 929 |
| | AS-CCC TTC CTC TTC CAG CTT CT | [SEQ ID NO:66] | | | |
| hEmx1 | S-CGT GTT CCC CGA GGC CAT GAA CCA | [SEQ ID NO:67] | | | |
| | AS-GAT GTC CTC CCC ATT GGC CTG CTT | [SEQ ID NO:68] | | | |
| mEmx2 #1 | S-CCG AGA GTT TCC TTT TGC ACA ACG C | [SEQ ID NO:69] | 310 | | — |
| | AS-GCC TGC TTG GTA GCA ATT CTC CAC C | [SEQ ID NO:70] | | | |
| mEmx2 #2 | S-CCC AGC TTT TAA GGC TAG AG | [SEQ ID NO:71] | 130 | | 929 |
| | AS-CTC CGG TTC TGA AAC CAT AC | [SEQ ID NO:72] | | | |
| hEmx2 | S-CGC CCA CCC CCT ACC CTC CTC | [SEQ ID NO:73] | | | |
| | AS-ACC CTG TGC CCT CGC TGT CCA | [SEQ ID NO:74] | | | |
| hEmx2 | S-CGC CCA CCC CCT ACC CTC CTC | [SEQ ID NO:73] | | | |
| | AS-ACC CTG TGC CCT CGC TGT CCA | [SEQ ID NO:74] | | | |
| SCL | S-TAT GAG ATG GAG ATT TCT GAT G | [SEQ ID NO:75] | | | |
| | AS-GCT CCT CTG TGT AAC TGT CC | [SEQ ID NO:76] | | | |
| mBcrp1 | S-CCA TAG CCA CAG GCC AAA GT | [SEQ ID NO:77] | 330 | | 930 |
| | AS-GGG CCA CAT GAT TCT TCC AC | [SEQ ID NO:78] | | | |
| CD34 | S-GGG TAT CTG CCT GGA ACT AA | [SEQ ID NO:79] | | | 937 |
| | AS-TTG CCA CCC AAC CAA ATC A | [SEQ ID NO:80] | | | |
| CD45 | S-ACC ATG GGT TTG TGG CTC AA | [SEQ ID NO:81] | | | 938 |
| | AS-GTA ATG TTC CCA AAC ATG GC | [SEQ ID NO:82] | | | |
| Sca-1 | S-ACT GTG CCT GCA ACC TTG TCT GAG A | [SEQ ID NO:83] | | | 932 |
| | AS-GTC CAG GTG CTG CCT CCA TT | [SEQ ID NO:84] | | | |
| c-Kit | S-GAA AGA CCA CAG CTT AAG ACT ACG GTC ACG | [SEQ ID NO:85] | | | 939 |
| | AS-ATG GAA TTC CTT ATG ATC ACA AAT GG | [SEQ ID NO:86] | | | |

TABLE 6

| | TARGET | HSA$^{lo}$PNA$^{lo}$ | | | HSA$^{hi}$PNA$^{lo}$ | | | HSA$^{lo}$PNA$^{hi}$ + HSA$^{hi}$PNA$^{hi}$ | | | Embryonic Neurospheres | | Postnatal Neurospheres | | Adult Neurosphers | |
|---|---|---|---|---|---|---|---|---|---|---|---|---|---|---|---|---|
| | | Sample 1 | Sample 2 | Sample 3 | Sample 1 | Sample 2 | Sample 3 | Sample 1 | Sample 2 | Sample 3 | Sample 1 | Sample 2 | Sample 1 | Sample 2 | Sample 1 | Sample 2 |
| GUIDANCE RECEPTORS | EphA4 | x | | | ✓ | | | ✓ | | | ✓ | ✓ | ✓ | ✓ | ✓ | ✓ |
| | DCC | ✓ | | | ✓ | | | ✓ | | | ✓ | ✓ | ✓ | ✓ | ✓ | ✓ |
| | Neogenin | ✓ | | | ✓ | | | ✓ | | | ✓ | ✓ | ✓ | ✓ | ✓ | ✓ |
| | Ryk | | | | | | | | | | | | | | | |
| NEUROTROPHIN RECEPTORS | p75 | ✓↓ | | | x | | | x | | | ✓ | ✓ | ✓ | ✓ | ✓ | ✓ |
| | TrkA | x | | | x | | | x | | | x | x | x | x | x | x |
| | TrkB | ✓↓ | | | x | | | x | | | ✓ | ✓ | ✓ | ✓ | ✓ | ✓ |
| | TrkC | x | | | x | | | ✓↓ | | | ✓ | ✓ | ✓ | ✓ | ✓ | ✓ |

TABLE 6-continued

| | TARGET | HSA$^{lo}$PNA$^{lo}$ | | | HSA$^{hi}$PNA$^{lo}$ | | | HSA$^{lo}$PNA$^{hi}$ + HSA$^{hi}$PNA$^{hi}$ | | | Embryonic Neurospheres | | Postnatal Neurospheres | | Adult Neurosphers | |
|---|---|---|---|---|---|---|---|---|---|---|---|---|---|---|---|---|
| | | Sample 1 | Sample 2 | Sample 3 | Sample 1 | Sample 2 | Sample 3 | Sample 1 | Sample 2 | Sample 3 | Sample 1 | Sample 2 | Sample 1 | Sample 2 | Sample 1 | Sample 2 |
| CYTOKINE RECEP | LIFRβ | x | | | x | | | x | | | ✓ | | ✓ | | ✓ | |
| | gp130 | x | | | x | | | x | | | ✓ | | ✓ | | ✓ | |
| DIFFERENTIATION RECEPTORS | Notch1 | ✓ | | | x | | | x | | | ✓ | | ✓ | | ✓ | |
| | Notch2 | ✓ | | | x | | | x | | | ✓ | | ✓ | | ✓ | |
| | Notch3 | ✓ | | | x | | | x | | | ✓ | | ✓ | | ✓ | |
| | Delta1 | x | | | x | | | x | | | ✓ | | ✓ | | ✓ | |
| TRA | SOCS1 | | | | | | | | | | | | | | | |
| | SOCS2 | x | | | x | | | x | | | ✓ | | ✓ | | ✓ | |
| | SOCS3 | x | | | x | | | x | | | ✓ | | ✓ | | ✓ | |
| | Pax6 | x | | | x | | | x | | | x | | ✓ | | ✓ | |
| | Tbr1 | x | | | x | | | x | | | ✓↓ | | x | | ✓↓ | |
| | Svec1 | | | | | | | | | | | | | | | |
| | Nkx2.1 | | | | | | | | | | | | | | | |
| | Dlx1 | ✓ | | | ✓ | | | x | | | ✓ | | ✓ | | ✓ | |
| | Dlx2 | x | | | x | | | x | | | ✓ | | ✓ | | ✓ | |
| | Sox1 | | | | | | | | | | | | | | | |
| | Sox2 | ✓ | | | ✓ | | | x | | | ✓ | | ✓ | | ✓ | |
| | Emx1 | | | | | | | | | | | | | | | |
| | Emx2 | | | | | | | | | | | | | | | |
| HAEMATOPOIETIC STEM CELL MARKERS | SCL | x | | | x | | | x | | | x | | x | | ✓ | |
| | Bcrp1 | x | | | x | | | x | | | ✓ | | ✓ | | ✓ | |
| | CD34 | | | | | | | | | | | | | | | |
| | CD45 | | | | | | | | | | | | | | | |
| | Sca-1 | x | | | x | | | x | | | x | | x | | x | |
| | c-Kjl | | | | | | | | | | | | | | | |

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

The invention claimed is:

1. A method for generating a substantially homogeneous population of undifferentiated neural stem cells (NSCs) which are phenotypically peanut agglutinin (PNA) low and heat stable antigen (HSA) low ($PNA^{lo}$ $HSA^{lo}$), from cells of the central nervous system (CNS), said method comprising subjecting said cells of the CNS to tissue-disruption means to provide a mixed population of cells comprising the undifferentiated cells to be purified, subjecting said mixed population of cells to cell size-discrimination means to generate a population of cells wherein substantially all cells are between 5 and 50 microns in size, and subjecting said population of cells to cell surface marker-discrimination means to generate a substantially homogeneous population of undifferentiated NSCs which are phenotypically $PNA^{lo}$ $HSA^{lo}$.

2. The method of claim 1, wherein said undifferentiated NSCs constitute at least about 50% of the cells of said substantially homogeneous population.

3. The method of claim 1 wherein the tissue-disruption means comprises dissociating individual cells from connecting extracellular matrix (ECM) tissue.

4. The method of claim 1 wherein the undifferentiated NSCs are from about 12 microns to about 50 microns.

* * * * *